United States Patent [19]

Ando

[11] Patent Number: 5,537,038

[45] Date of Patent: Jul. 16, 1996

[54] MAGNETIC FLUX MEASURING METHOD AND APPARATUS FOR DETECTING HIGH FREQUENCY COMPONENTS OF MAGNETIC FLUX WITH HIGH SPEED ORIENTATION

[75] Inventor: Seigo Ando, Tokyo, Japan

[73] Assignee: NKK Corporation, Tokyo, Japan

[21] Appl. No.: 389,979

[22] Filed: Feb. 14, 1995

Related U.S. Application Data

[63] Continuation of Ser. No. 74,998, Jun. 11, 1993, abandoned, which is a continuation of Ser. No. 640,684, Jan. 14, 1991, abandoned, which is a continuation-in-part of Ser. No. 449,986, Dec. 12, 1989, abandoned.

[30] Foreign Application Priority Data

| Dec. 15, 1988 | [JP] | Japan | 63-162871 U |
|---|---|---|---|
| Apr. 28, 1989 | [JP] | Japan | 1-110109 |
| Feb. 28, 1990 | [JP] | Japan | 2-47822 |
| May 2, 1990 | [JP] | Japan | 2-115284 |
| Oct. 19, 1990 | [JP] | Japan | 2-278918 |

[51] Int. Cl.$^6$ ............ G01R 33/04; G01R 33/12; G01N 27/82
[52] U.S. Cl. ............ 324/253; 324/234; 324/237
[58] Field of Search .......... 324/253, 254, 324/255, 234, 236, 237, 238, 260, 262; 33/361

[56] References Cited

U.S. PATENT DOCUMENTS

| 2,938,164 | 5/1960 | Hansburg ............ 324/255 |
|---|---|---|
| 3,246,219 | 4/1966 | Devol et al. . |
| 3,617,874 | 11/1971 | Forster . |
| 3,854,085 | 12/1974 | Mansson . |
| 4,300,095 | 11/1981 | Rhodes . |
| 4,303,886 | 12/1981 | Rhodes . |
| 4,305,035 | 12/1981 | Mach et al. . |
| 4,321,536 | 3/1982 | Rhodes . |
| 4,402,034 | 8/1983 | Parker et al. . |
| 4,503,305 | 3/1985 | Kratzer et al. . |
| 4,728,888 | 3/1988 | Bauer et al. . |
| 4,972,146 | 11/1990 | Eckardt et al. ............ 324/255 |

FOREIGN PATENT DOCUMENTS

| 30-2590 | 4/1955 | Japan . |
|---|---|---|
| 30-4291 | 6/1955 | Japan . |
| 51-47469 | 4/1976 | Japan . |
| 2169710 | 7/1986 | United Kingdom . |
| WO88/03654 | 5/1988 | WIPO ............ 324/253 |

OTHER PUBLICATIONS

"Magnetic Modulators" Electronics Feb. 1952; pp. 113–117.
"Airborne Equipment For Geomagnetic Measurement", vol. 30, No. 6, Dec. 1949; pp. 836–848.

Primary Examiner—Walter E. Snow
Attorney, Agent, or Firm—Frishauf, Holtz, Goodman, Langer & Chick

[57] ABSTRACT

A current of predetermined frequency is fed to a coil wound around a ferromagnetic core through a fixed impedance means. A magnetic flux measurement is performed in terms of a level of a DC component of a voltage generated across the coil. A DC bias is added to the current of predetermined frequency, and the resultant current is applied through the fixed impedance means to the coil wound around the ferromagnetic core. A magnetic flux measurement is performed in terms of a level of a DC component of the voltage across the coil. A magnetic flux measuring method and apparatus for embodying the same have a high sensitivity in detecting a minute magnetic flux and an improved temperature characteristic because an output voltage little varies against a temperature variation. A magnetic flux measuring method and apparatus for embodying the same, when they are applied to a leakage flux flaw detection using a saturable magnetic flux sensor, is capable of expanding a measuring span of the magnetic flux sensor, thereby to improve a flaw detection performance.

9 Claims, 35 Drawing Sheets

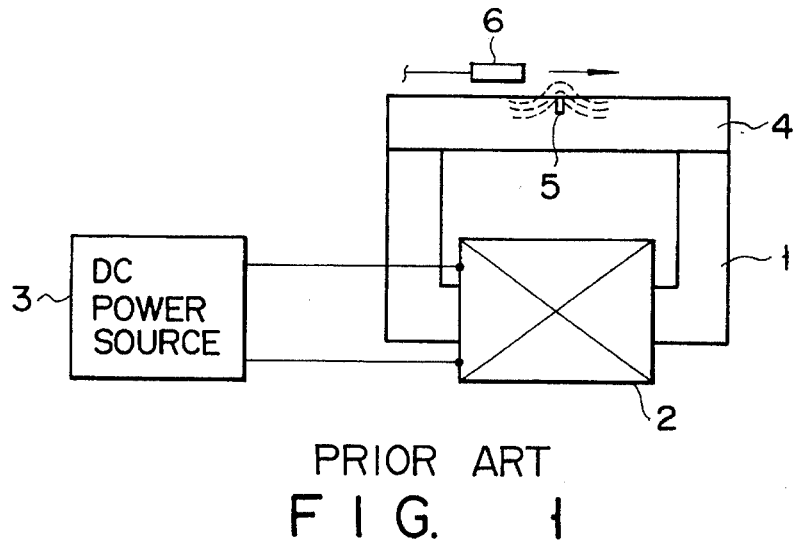
PRIOR ART
FIG. 1
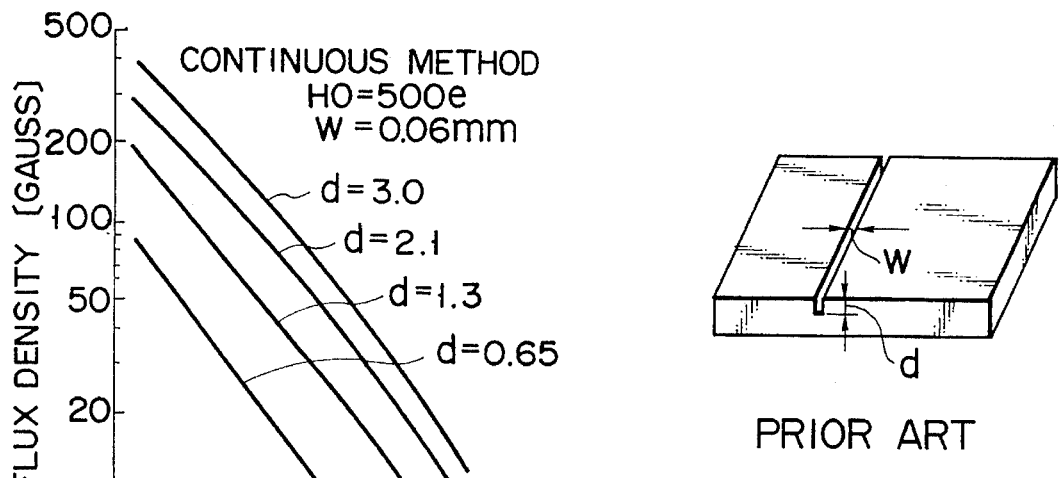
PRIOR ART
FIG. 3
DISTANCE OF THE SURFACE OF A
STEEL MATERIAL AND A HALL DEVICE [mm]
HO: MAGNETIC FIELD APPLIED TO
    THE STEEL MATERIAL
W: WIDTH OF A FLAW
d: DEPTH OF THE FLAW [mm]
PRIOR ART
FIG. 2

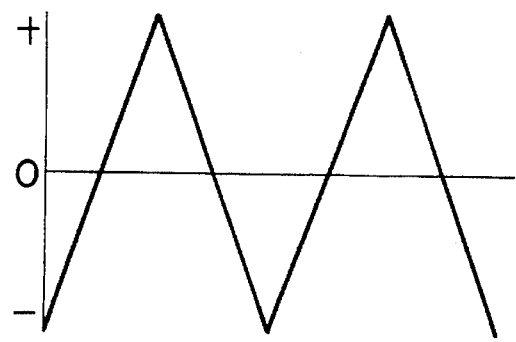
F I G. 9A
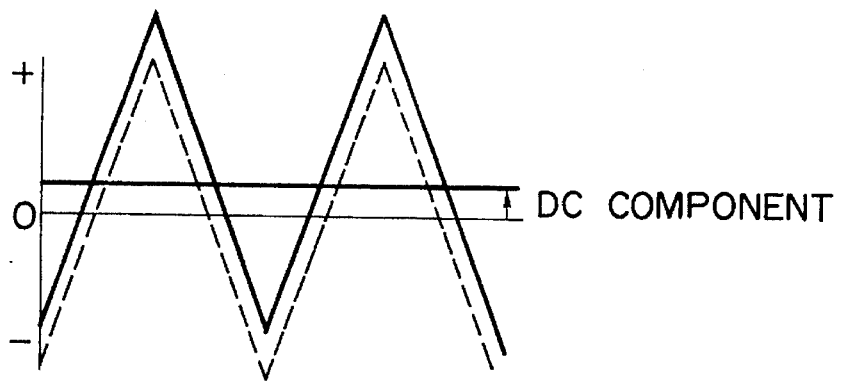
DC COMPONENT
F I G. 9B
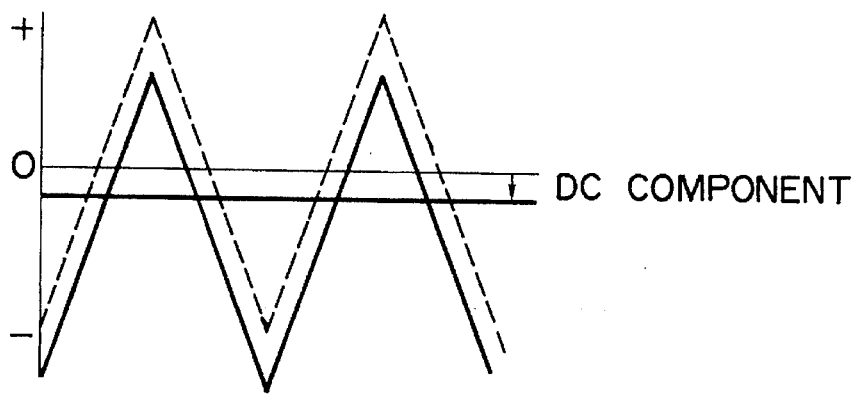
DC COMPONENT
F I G. 9C

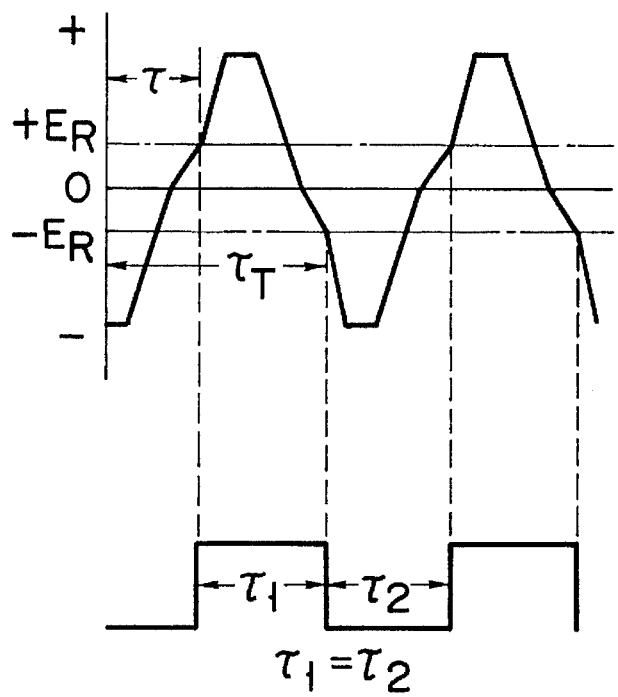
FIG. 11A
FIG. 11B
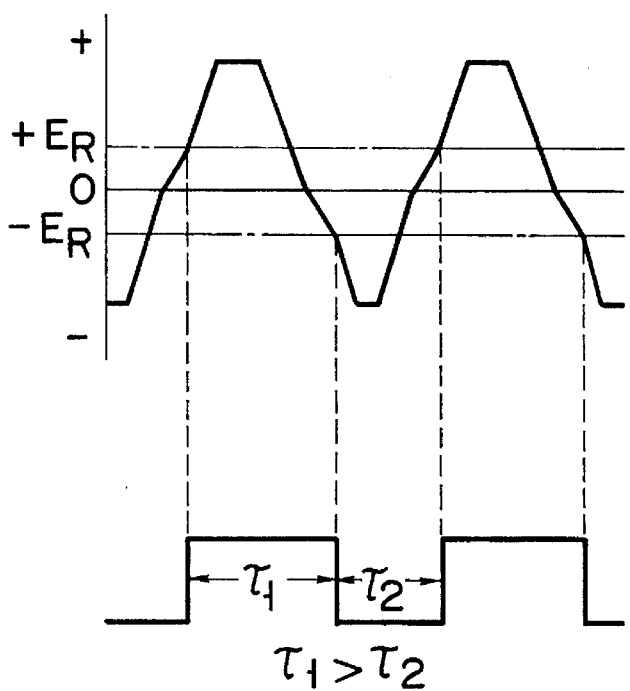
FIG. 11C
FIG. 11D

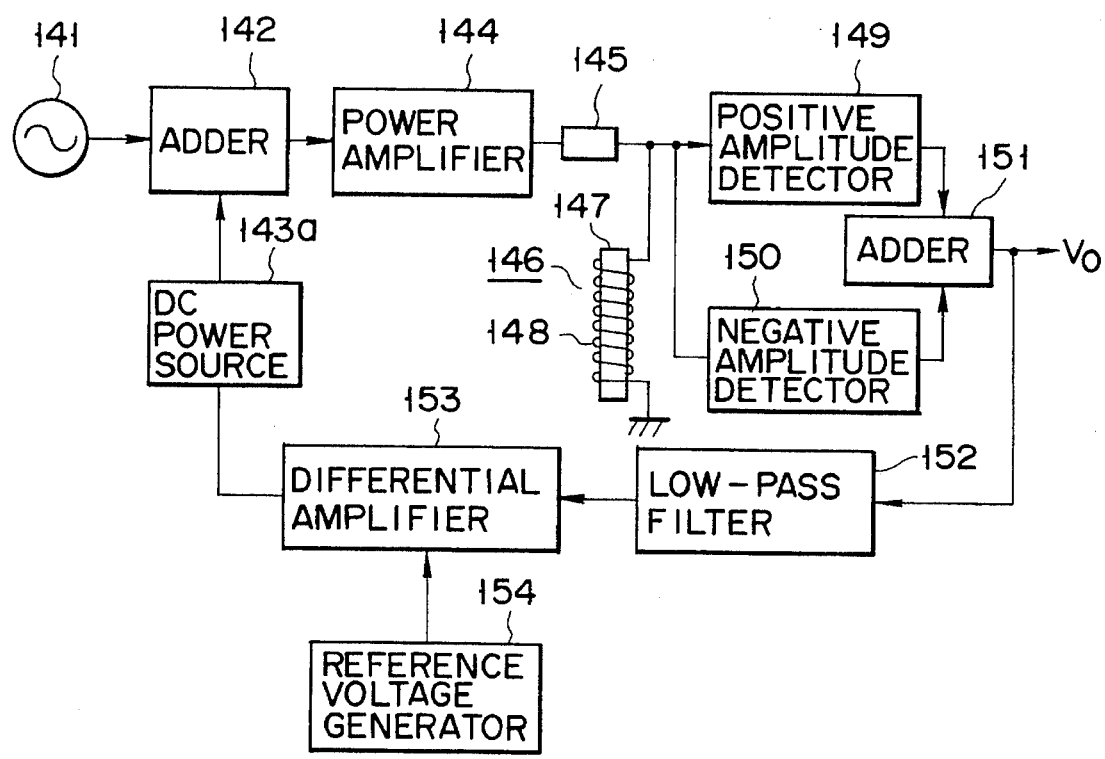
F I G. 30

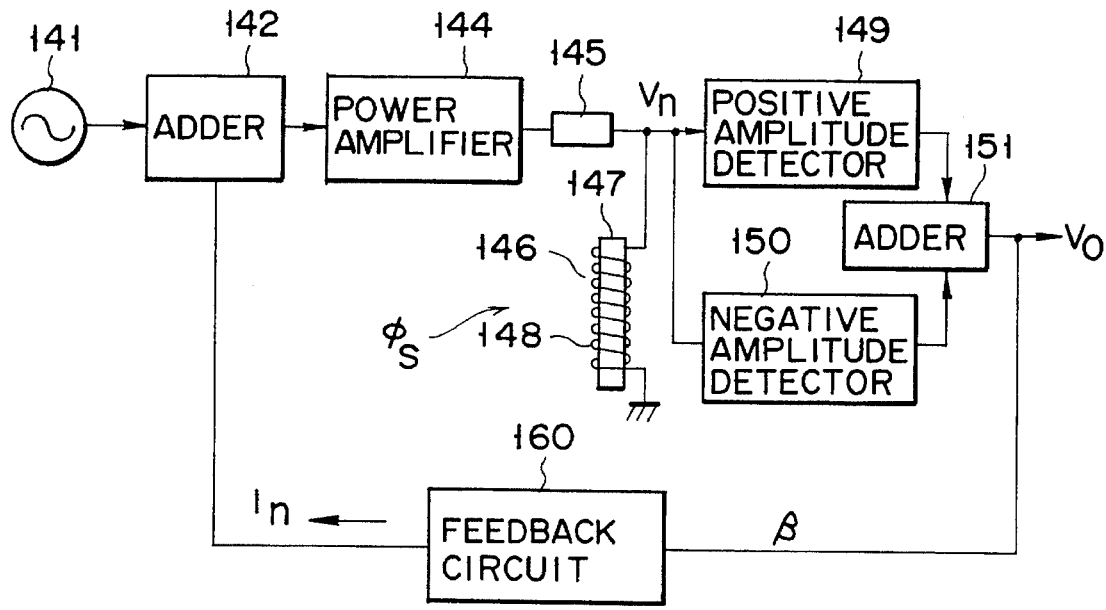
F I G. 31
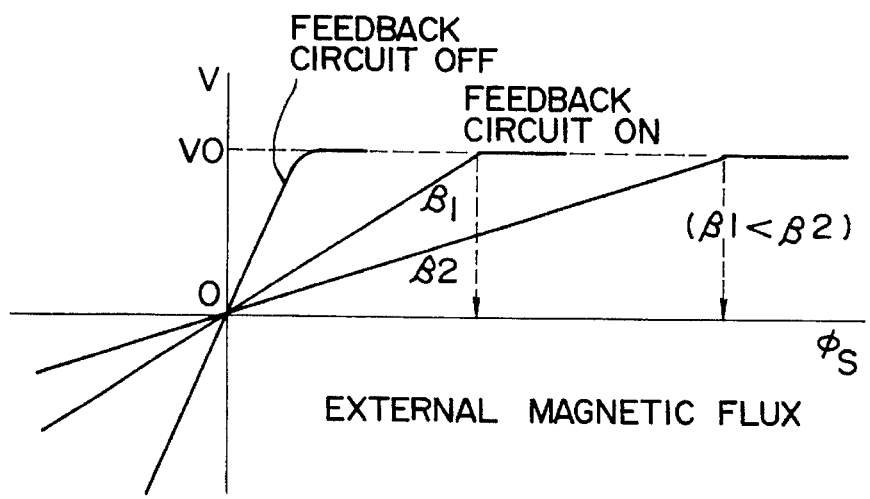
F I G. 32

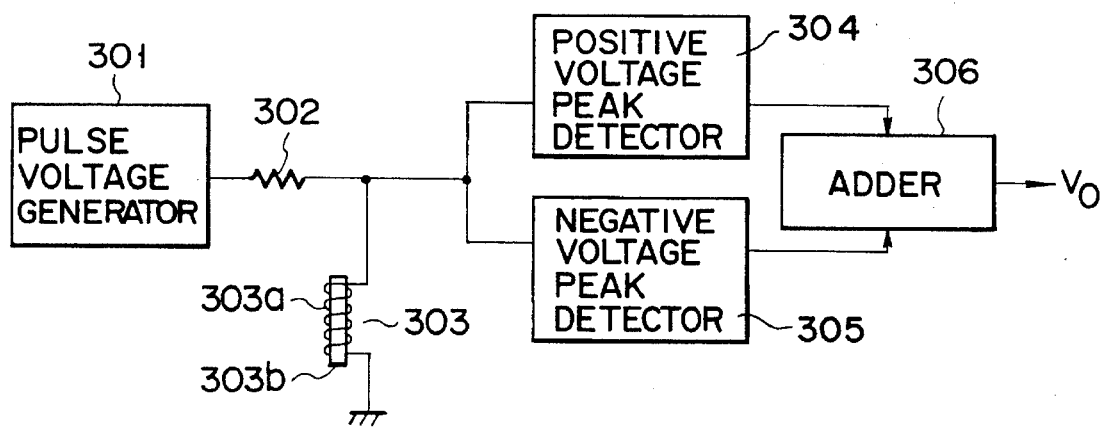
F I G. 35
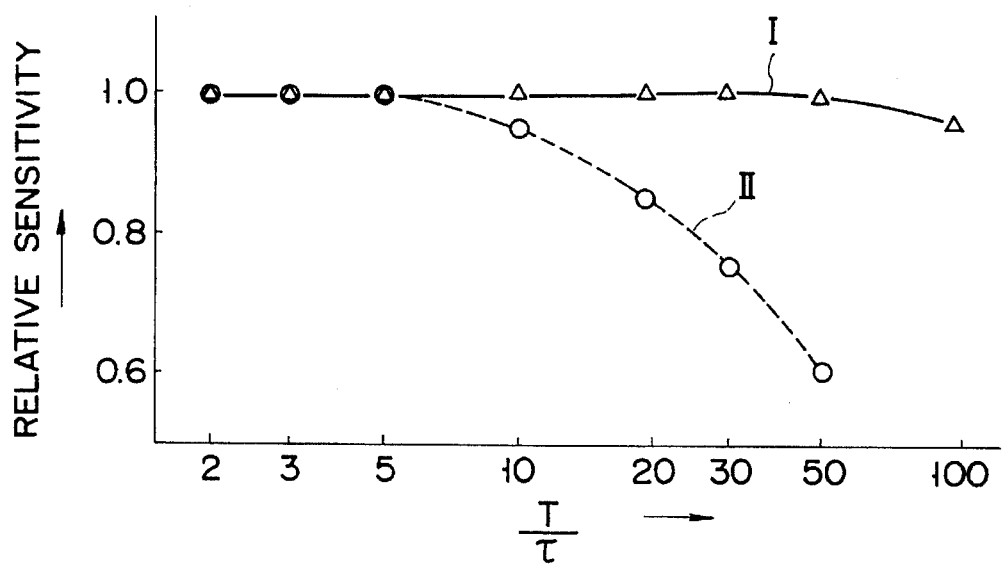
F I G. 36

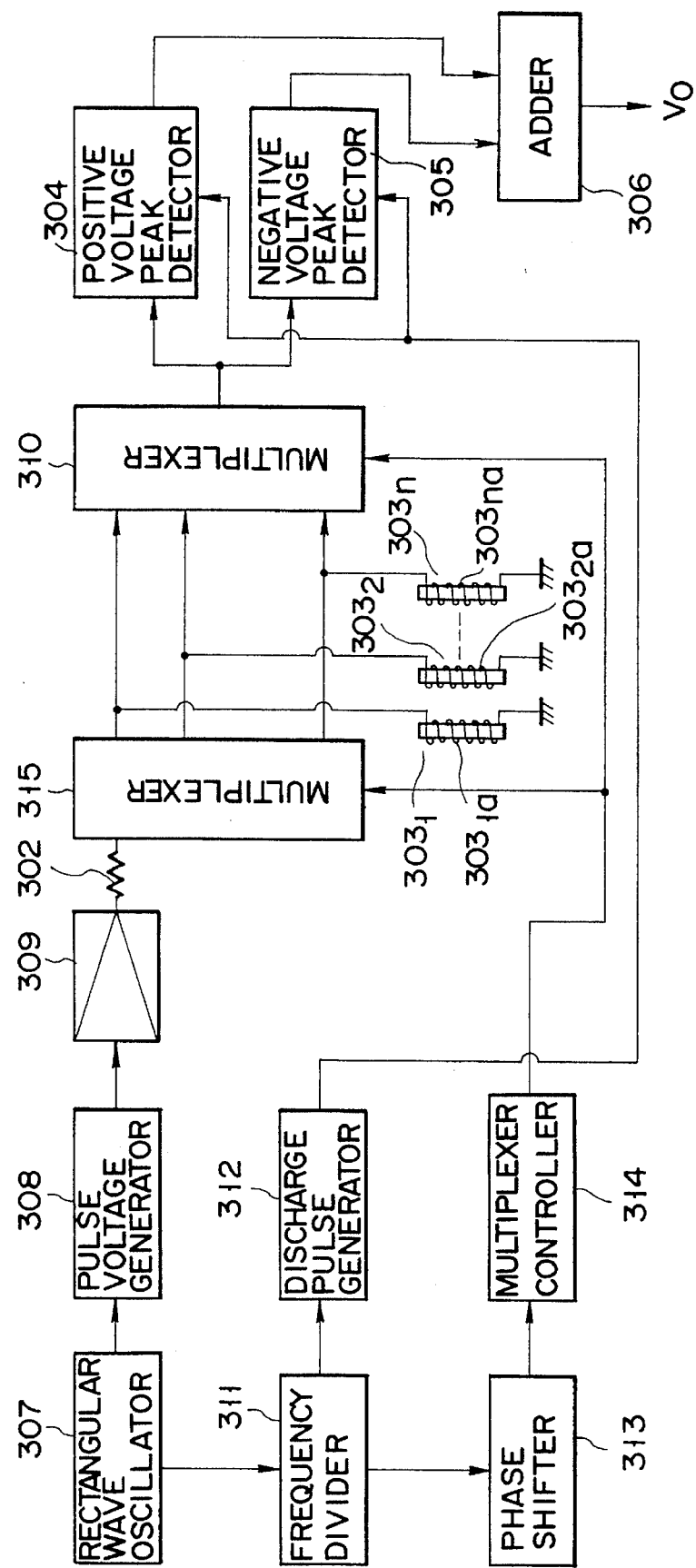
F I G. 39

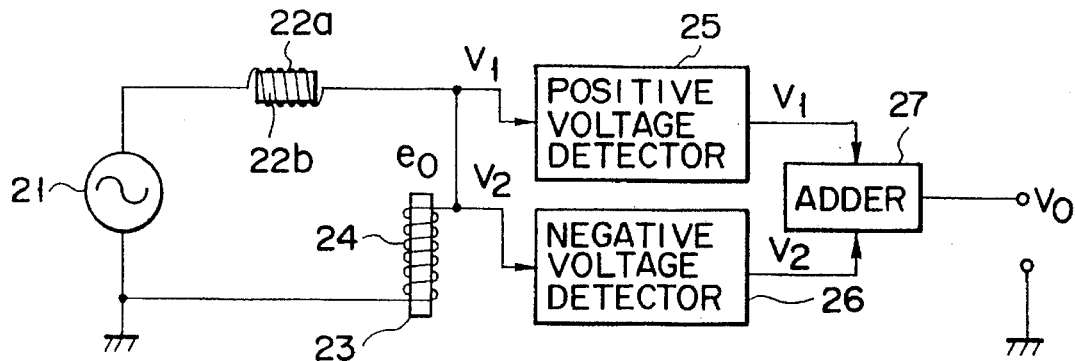
F I G. 40
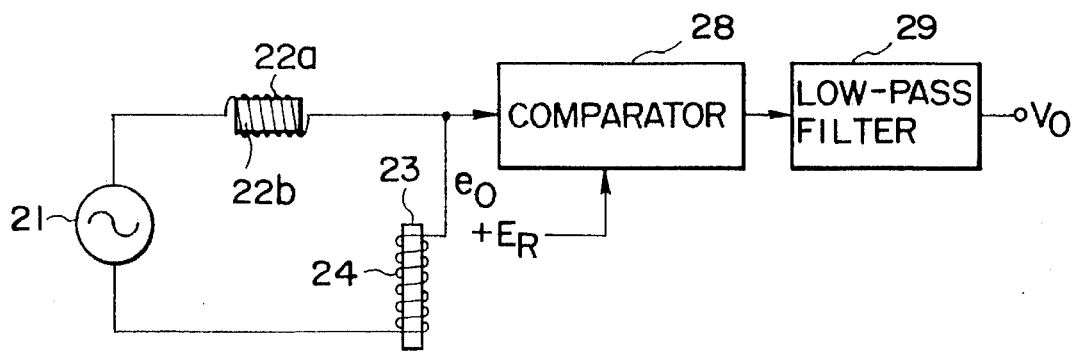
F I G. 41
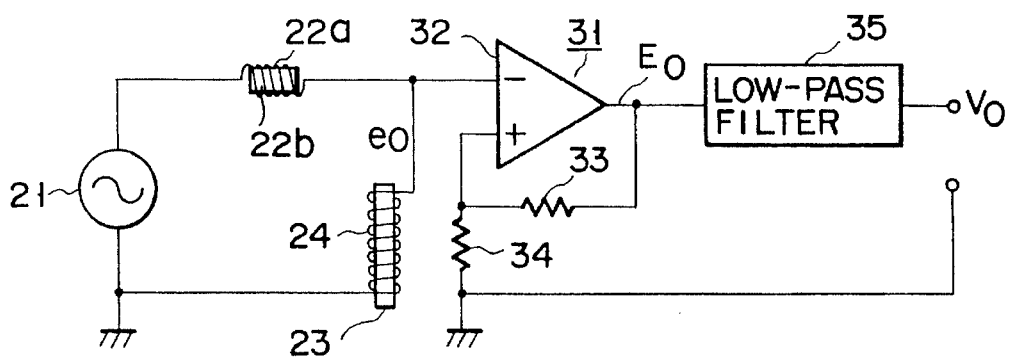
F I G. 42

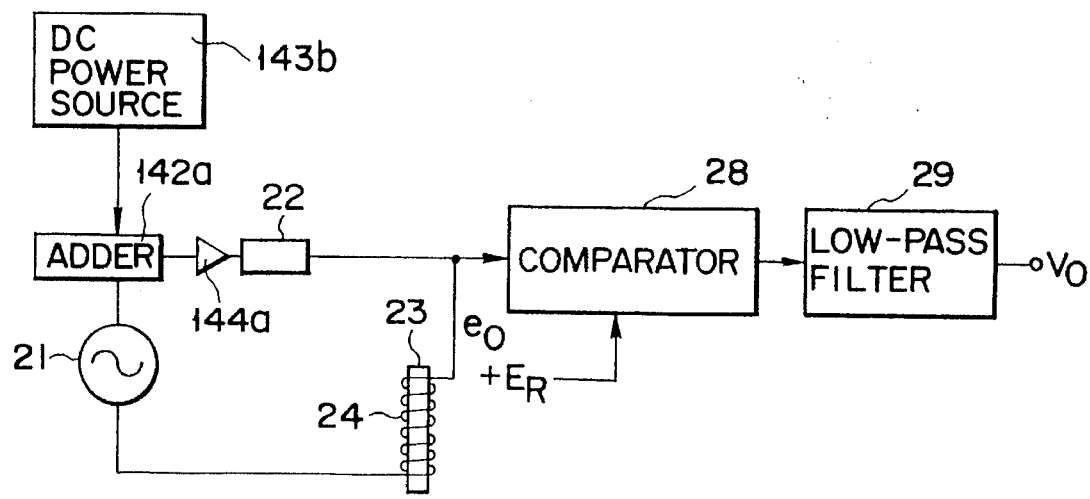
F I G. 43
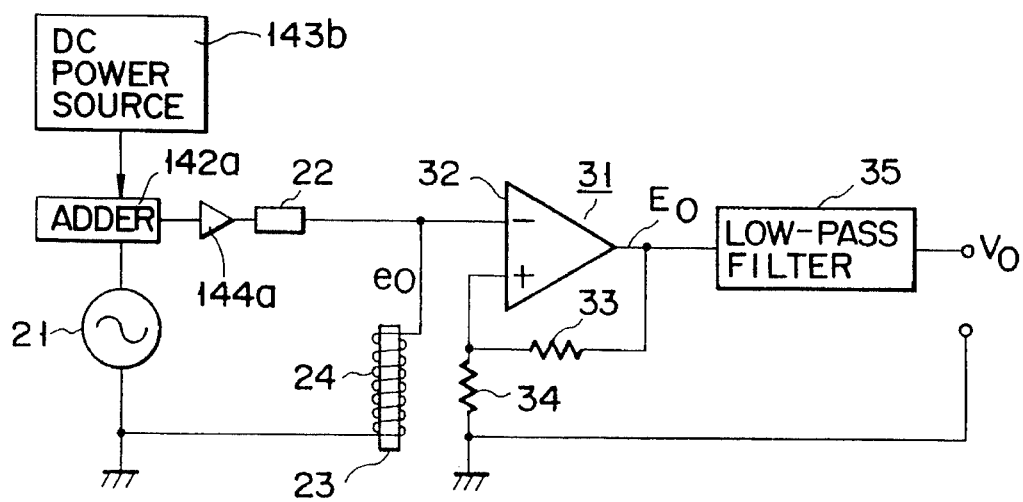
F I G. 44

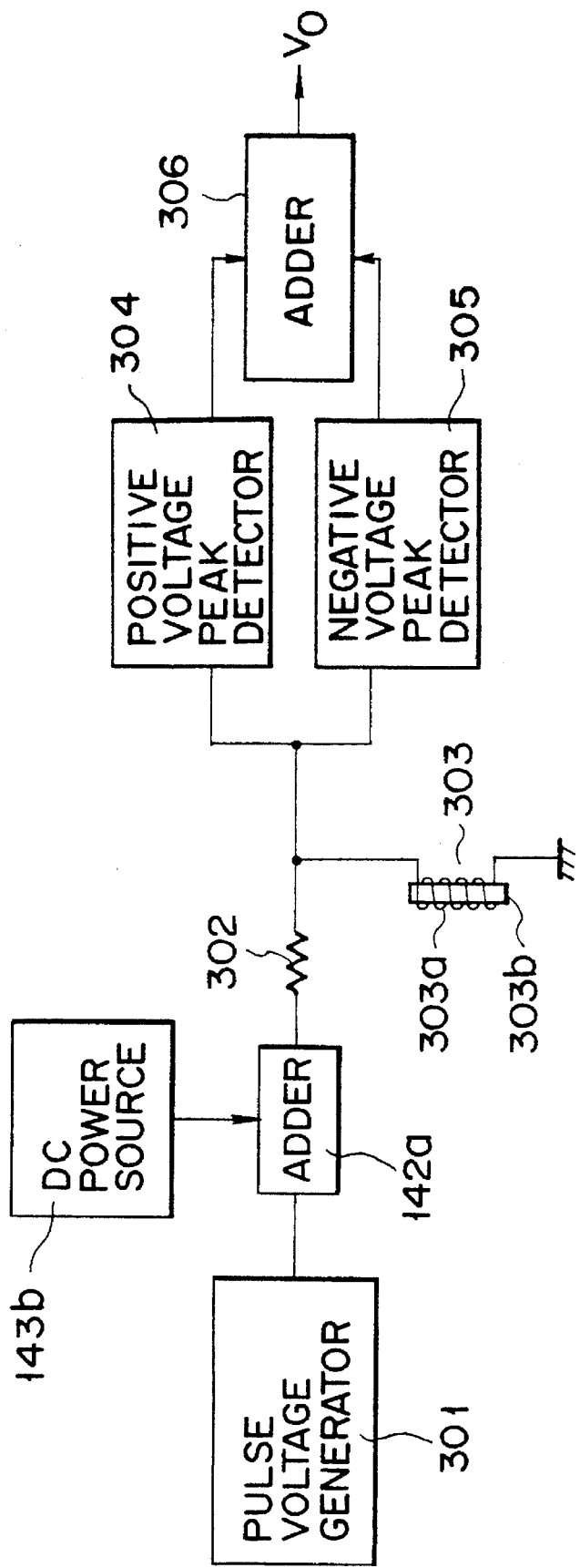
F I G. 45

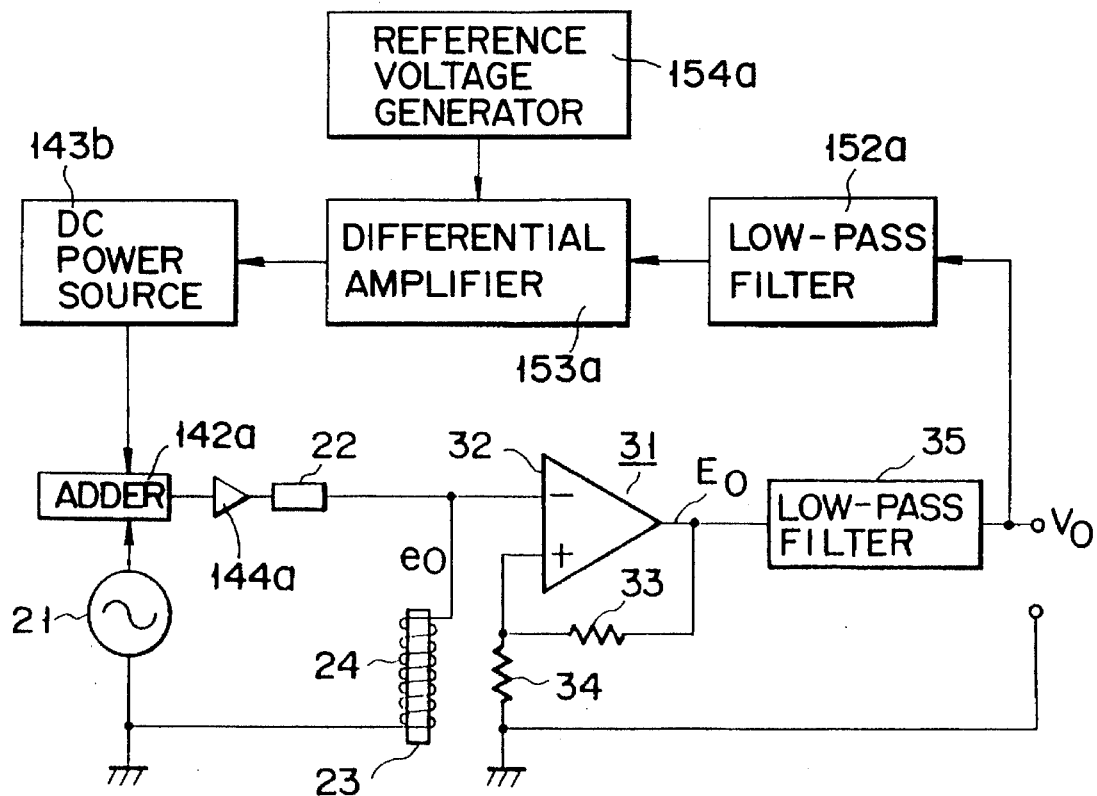
F I G. 47

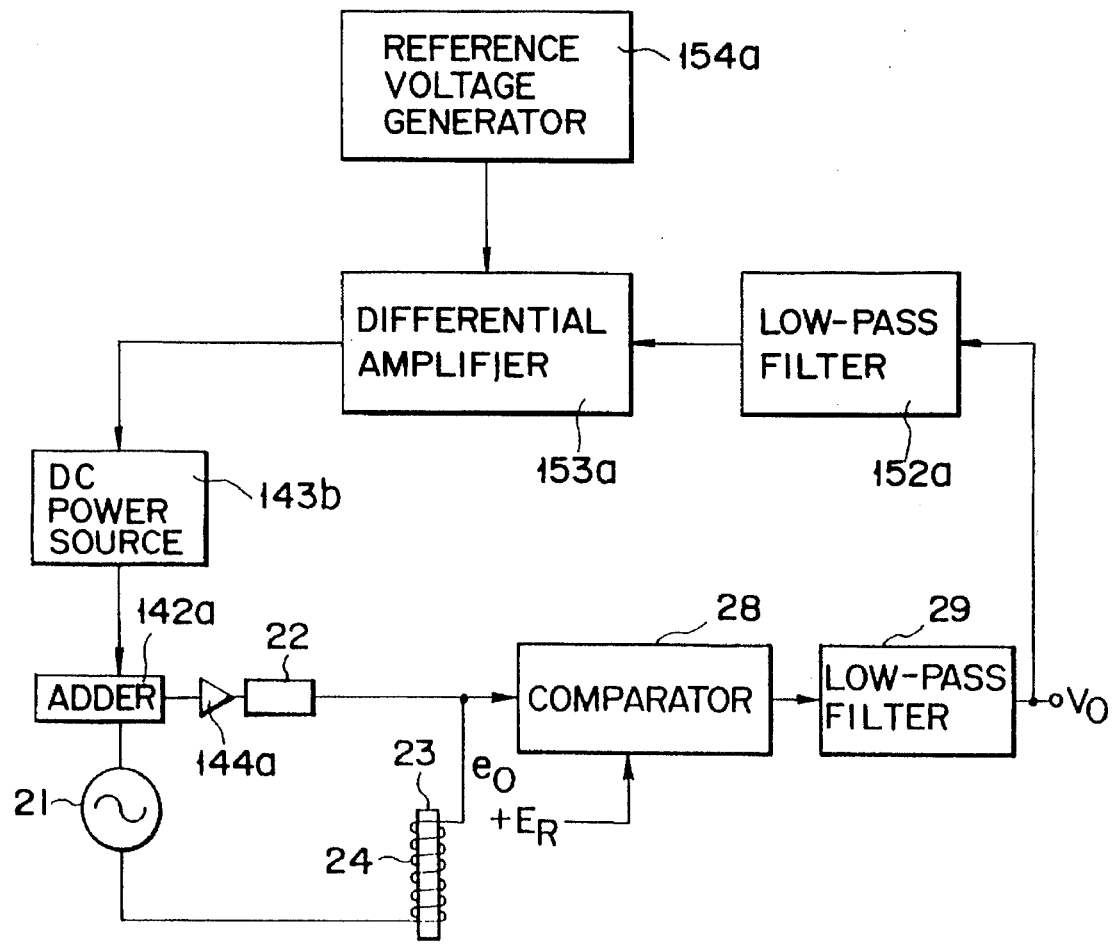
F I G. 49

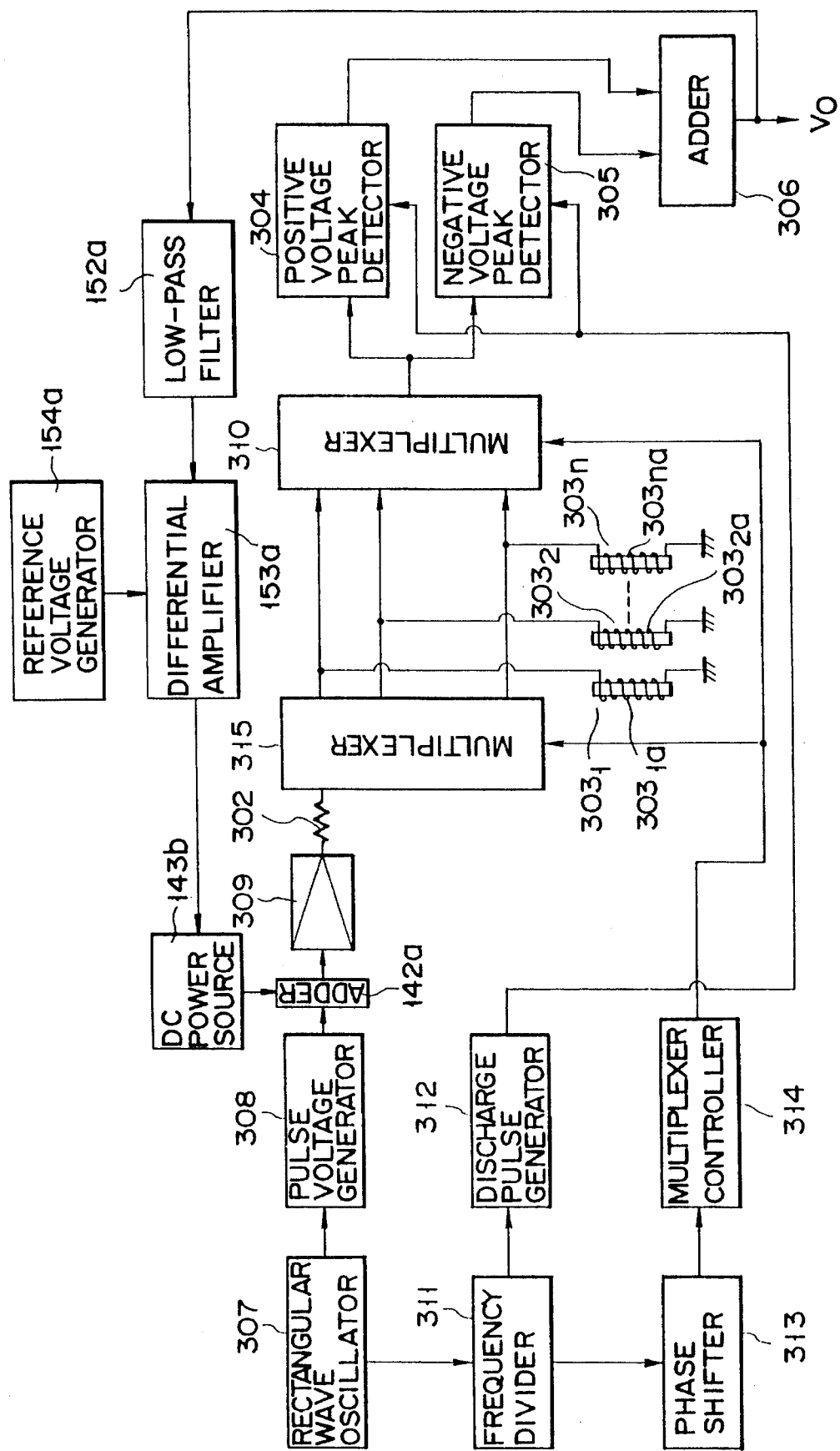
F I G. 50

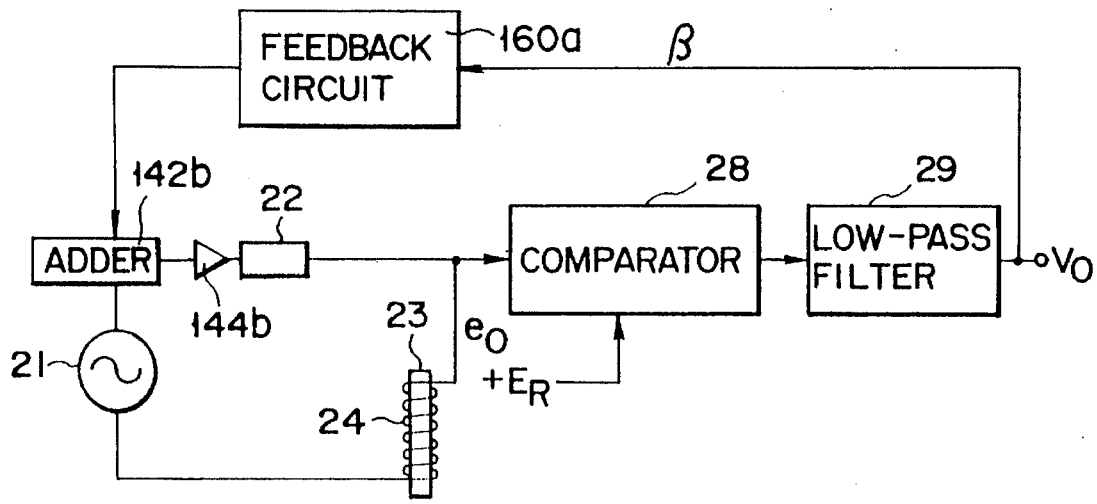
F I G. 51
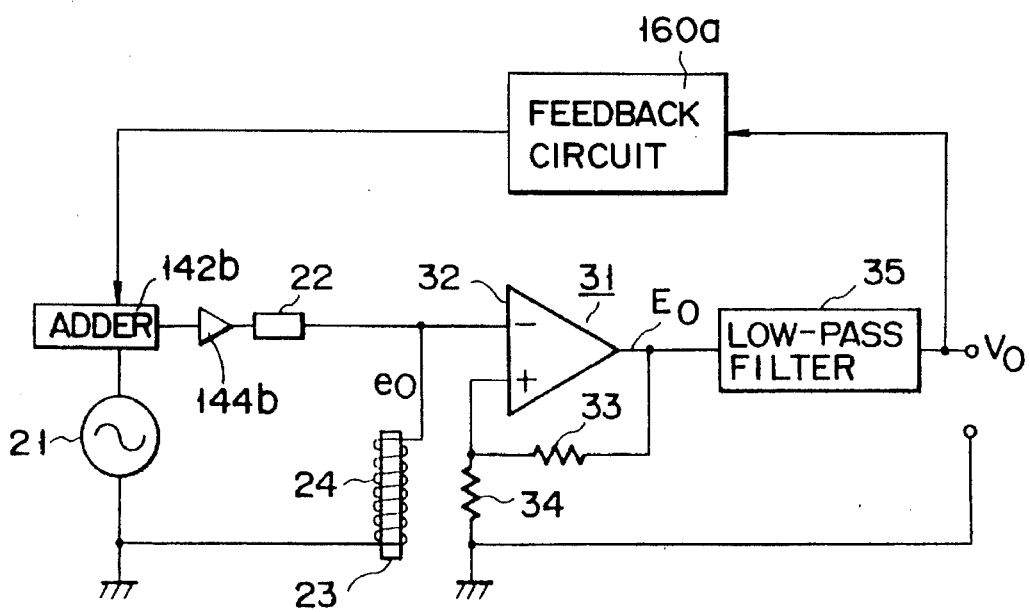
F I G. 52

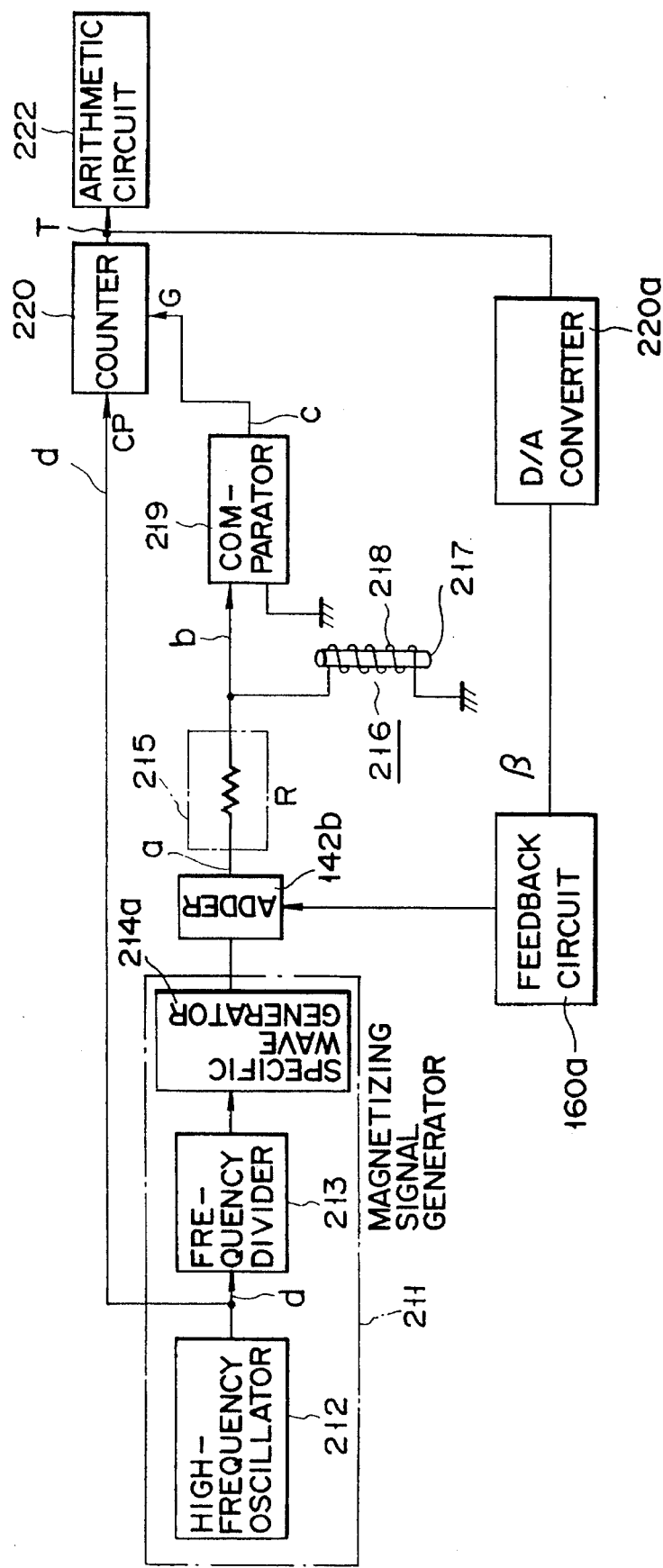
F I G. 53

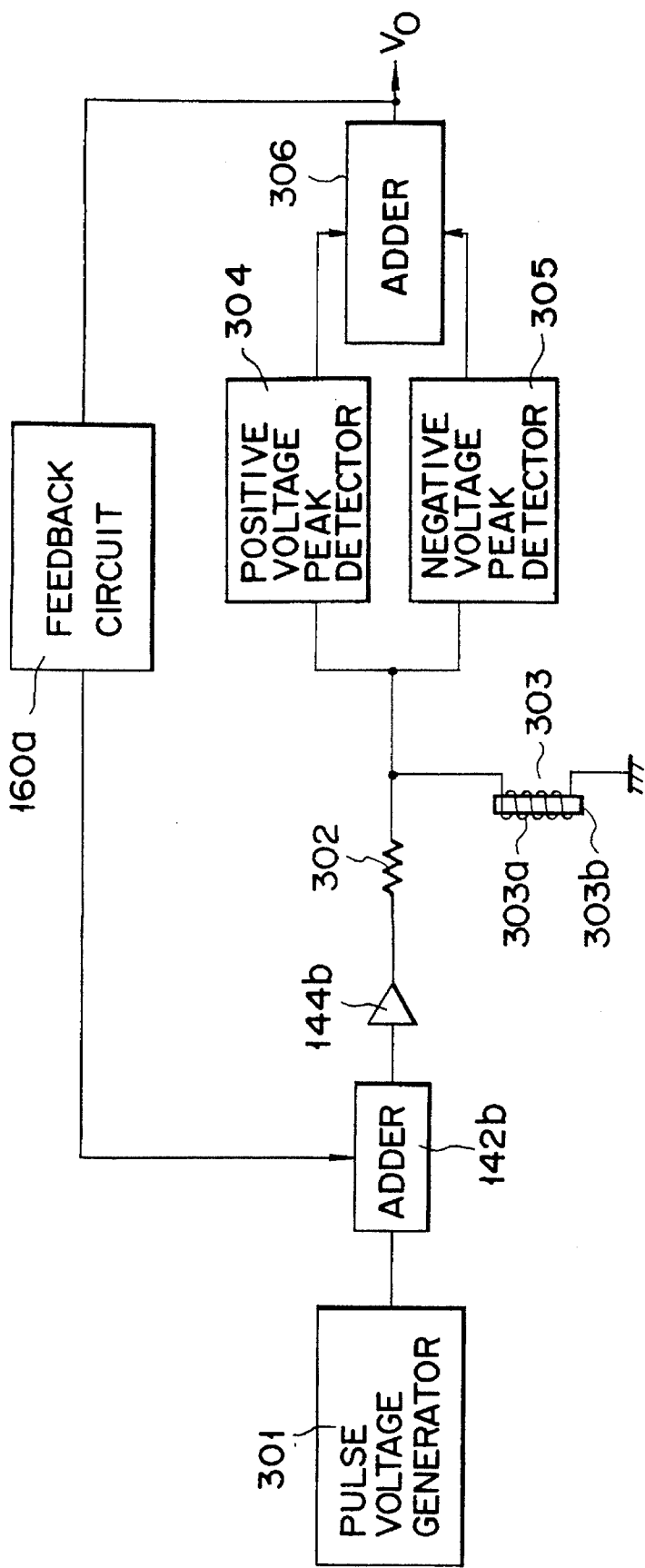
F I G. 54

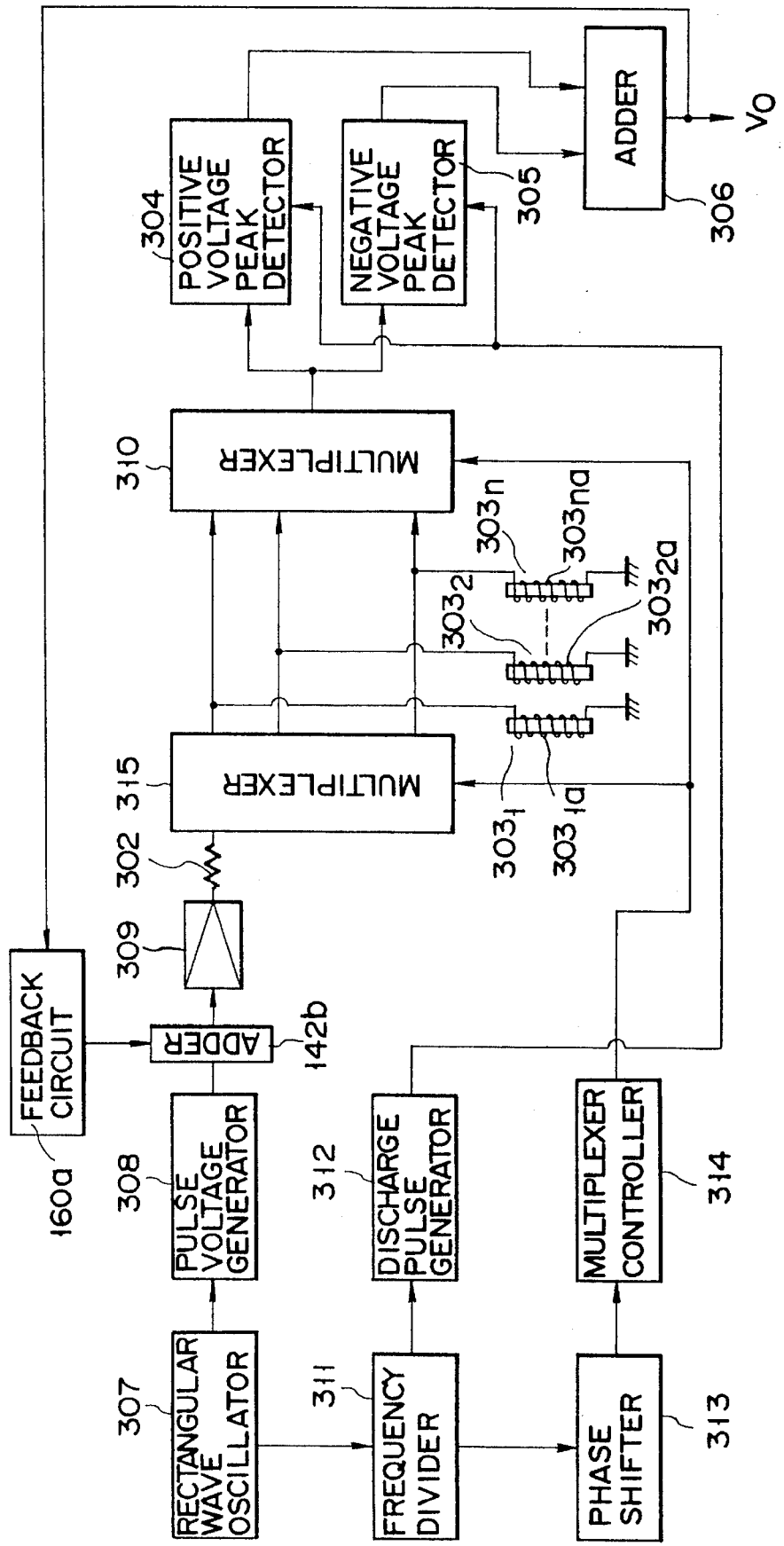
F I G. 56

MAGNETIC FLUX MEASURING METHOD AND APPARATUS FOR DETECTING HIGH FREQUENCY COMPONENTS OF MAGNETIC FLUX WITH HIGH SPEED ORIENTATION

This application is a Continuation of application Ser. No. 08/074,998, filed Jun. 11, 1993 (now abandoned) which is a Continuation of prior application Ser. No. 07/640,684 filed on Jan. 14, 1991 (now abandoned) which was a Continuation-in-Part of application Ser. No. 07/449,986 filed Dec. 12, 1989 (now abandoned).

BACKGROUND OF THE INVENTION

1. Field of the Invention

The present invention relates to a minute magnetic flux measuring method and apparatus for embodying the same, which are adaptable for, for example, a leakage flux flaw detection.

2. Description of the Related Art

A method for detecting a flaw of a steel pipe, a steel plate, etc., may come in three varieties, an ultrasonic flaw detecting method, an eddy current flaw detecting method, and a leakage flux flaw detecting method. Of those methods, the leakage flux flaw detecting method is relatively widely used, because it can detect flaws in both sides of a thick steel plate from a single side, and it has a high sensitivity in detecting flaws in the innards of a steel pipe.

A typical known technique of the leakage flux flaw detecting method will be described. As shown in FIG. 1, a DC power source 3 supplies a DC power to a coil 2 wound around a magnetizing yoke 1. A test piece 4 to be detected is put on the magnetizing yoke 1 and is magnetized there. If the detected test piece 4 contains a flaw 5, a magnetic flux partially leaks outside of the test piece 4 from the flaw 5, as indicated by dotted lines. A magnetic flux sensor 6 detects the leakage flux and converts it into an electrical signal. In this way, the flaw 5 is detected in an indirect manner. The leakage flux emanating from the flaw 5 is very weak as shown in FIG. 2, which graphically illustrate relationships between the leakage flux and a distance between the surface of a steel material and Hall device as the magnetic flux sensor. FIG. 3 shows a steel material to be used for a measurement in FIG. 2. In the figure, W indicates the width of the flaw and "d", the depth of the flaw.

From this fact, it is seen that the requirements for the magnetic flux sensor 6 for detecting the leakage flux are: 1) The sensitivity of the magnetic flux sensor for a weak magnetic field is high. 2) The initial bias voltage of the sensor little varies. 3) The temperature characteristic of the sensor is good.

A sensitivity of the magnetic flux sensor now marketed, however, is very small as shown in FIG. 4. In the figure, a line "a" indicates a sensitivity of a magneto-diode as a magnetic flux sensor; a line "b", that of a magneto-resistive sensor; a line "c", that of a Hall device.

A variation of the initial bias voltages of twelve magneto-resistive flux sensors is as shown in FIG. 5. Even if a nondefective portion (free from any defect) of the test piece 4 is magnetized, a leakage flux is detected from the nondefective portion. This leakage flux is called as initial bias voltages. As see from the graph, the initial bias voltages of the sensors are greatly different from one another. Therefore, before use, the initial bias voltage must be adjusted for every sensor; otherwise when the detected signal is amplified, the amplifier using the sensor of the low initial bias voltage is saturated, and consequently the flaw detector is inoperative for flaw detection.

A temperature characteristic of a magneto-diode 7 has been obtained, as platted in FIG. 7, when the output voltage of the magneto-diode 7 is measured by using a circuit in which a magneto-diode 7 is connected through a resistor 8 to a DC power source 9, as shown in FIG. 6. As seen, a rate of change of an output voltage of the sensor against temperature is great.

SUMMARY OF THE INVENTION

Accordingly, an object of the present invention is to provide a minute magnetic flux measuring method and apparatus for embodying the same which are sensitive to a minute magnetic field, but insensitive to temperature variation.

It is another object of the present invention to provide a minute magnetic flux measuring apparatus wherein an AC magnetizing current having a predetermined root-mean-square value (RMS) is applied to a detection coil of a magnetic sensor to obtain a detection signal, thereby greatly reducing a voltage value of the AC magnetizing electric power applied to the magnetic sensor, and an external magnetic field intensity can be easily detected from a rate of change in width of a signal waveform of the detection signal, thereby simplifying a circuit arrangement of the apparatus as a whole and making the apparatus compact at low cost.

It is still another object of the present invention to provide a battery-driven minute magnetic flux measuring method and an apparatus for embodying the same, wherein a detection sensitivity for a minute magnetic field can be increased, and the coil of the magnetic sensor can be driven with a pulse voltage.

It is still another object of the present invention to provide a battery-driven minute magnetic flux measuring apparatus, wherein a coil of each magnetic sensor is driven with a pulse voltage even if a large number of magnetic sensors is used, and voltages generated by the coils are sequentially and alternatively extracted, thereby achieving an energy-saving arrangement.

According to one aspect of the present invention, there is provided a minute magnetic flux measuring method, comprising the steps of: supplying through a fixed impedance an AC current of a predetermined frequency to a coil wound around one ferromagnetic core; generating an AC voltage across said coil upon supply of the AC current; detecting positive and negative waveforms of the AC voltage; comparing the positive waveform with the negative waveform; and measuring a DC component voltage corresponding to an external magnetic flux crossing said coil.

According to another aspect of the present invention, there is provided a minute magnetic flux measuring apparatus comprising: a coil wound around one ferromagnetic core; a power sower for supplying an AC current of a predetermined frequency to a coil through a fixed impedance and for causing said coil to generate an AC voltage; and means for detecting a positive waveform of the AC voltage and a negative waveform thereof, comparing the positive waveform with the negative waveform, and outputting a voltage corresponding to the external magnetic flux crossing said coil.

According to still another aspect of the present invention, there is provided a minute magnetic flux measuring apparatus comprising: a coil wound around one ferromagnetic core; a power source for supplying an AC current of a predetermined frequency to said coil through a fixed impedance and generating an AC voltage across said coil; a level discriminator for generating a voltage signal of high level suitable for a positive reference voltage in which a positive waveform of the AC voltage is preset, and for generating a voltage signal of 1 level when a negative waveform of the AC voltage reaches the preset negative reference voltage; and means for comparing pulse widths of the voltage signals output from said level discriminator.

According to still another aspect of the present invention, there is provided a minute magnetic flux detecting apparatus comprising: a magnetic sensor including a core consisting of a ferromagnetic material and a detection coil wound around said core; a magnetizing signal generator for supplying an AC magnetizing current having a predetermined root-mean-square value to said detection coil of said magnetic sensor through an impedance element to magnetize said core to a saturation range; a waveshaper for normalizing a waveform of a detection signal extracted across said detection coil, with a predetermined threshold value; and a counter for measuring a pulse width of a normalized signal output from said waveshaper, wherein an intensity of the external magnetic flux is detected in accordance with a change in the pulse width caused by crossing between the external magnetic field and said magnetic sensor.

According to still another aspect of the present invention, there is provided a minute magnetic flux detecting apparatus comprising: a magnetic sensor including a core consisting of a ferromagnetic material and a detection coil wound around said core; a magnetizing signal generator for supplying an AC magnetizing current having a predetermined root-mean-square value to said detection coil of said magnetic sensor through an impedance element to magnetize said core to a saturation range; a waveshaper for normalizing a waveform of a detection signal extracted across said detection coil, with a predetermined threshold value; and a low-pass filter for detecting the pulse width of a normalized signal output from said waveshaper as an average DC component, wherein an intensity of the external magnetic field is detected by a change in the pulse width caused by crossing between the external magnetic flux and said magnetic sensor.

According to yet another aspect of the present invention, there is provided a minute magnetic flux measuring method, wherein a magnetic sensor obtained by winding a coil around a ferromagnetic core is caused to come close to a target magnetic field, positive and negative pulse voltages are supplied to said coil of said magnetic sensor through a fixed impedance, positive and negative peak values of a voltage generated across said coil are detected, the positive and negative peak values are added to each other, and a sum is defined as a measurement value corresponding to the target magnetic field.

According to yet another aspect of the present invention, there is provided a minute magnetic flux measuring apparatus comprising: a magnetic sensor including a ferromagnetic core and a coil wound around said ferromagnetic core; a pulse voltage supply source for supplying positive and negative pulse voltages to said coil of said magnetic sensor through a fixed impedance; a pair of peak value detecting means for respectively detecting positive and negative peak values of a voltage generated across said coil; and an adder for adding the positive and negative peak values detected by said pair of said peak value detecting means and outputting a measurement value.

According to yet another aspect of the present invention, there is provided a minute magnetic flux measuring apparatus comprising: a plurality of magnetic sensors each including a ferromagnetic core and a coil wound around said ferromagnetic core; a pulse voltage supply source for applying positive and negative pulse voltages to said coil of each magnetic sensor through a fixed impedance; selecting means for sequentially and alternatively extracting voltages generated across said coils; a pair of peak value detecting means for respectively detecting positive and negative peak values sequentially extracted by said selecting means; and an adder for adding the positive and negative peak values of each voltage detected by said peak value detecting means and generating a measurement value corresponding to each magnetic sensor.

According to yet another aspect of the present invention, there is provided a minute magnetic flux measuring apparatus comprising: a plurality of magnetic sensors each including a ferromagnetic core and a coil wound around said ferromagnetic core; a pulse voltage supply source for applying positive and negative pulse voltages to said coil of each magnetic sensor through a fixed impedance; selecting means for sequentially and alternatively extracting voltages generated across said coils in synchronism with supply of the pulse voltage from said voltage supply source to each coil; a pair of peak value detecting means for respectively detecting positive and negative peak values sequentially extracted by said selecting means; and an adder for adding the positive and negative peak values of each voltage detected by said peak value detecting means and generating a measurement value corresponding to each magnetic sensor.

The principles of the present invention will be described. As shown in FIG. 8, an oscillator 11 as a power source at predetermined frequency and voltage is connected in series to a fixed impedance 12 and a coil 14 wound around a ferromagnetic core 13. In the series connection circuit, when the oscillator 11 supplies an AC power of a waveform as shown in FIG. 9A to the coil 14, a voltage generated across the coil 14 depends on a resistive value R of the fixed impedance 12 and an impedance Zs of the coil 14, as given by $$e_o = e \cdot Zs/(R+Zs)$$

where $e_o$=voltage across the coil 14, and e=output voltage of the oscillator 11.

An impedance of the coil 14 varies in proportion to a magnetic permeability of the core 13 because it is wound around the core 13. Let us consider that an AC current is fed to the coil 14 in a state that a magnet 15 for producing an external magnetic field is separated from the core 13, that is, no external magnetic field is applied to the core 13. At this time, a magnetic permeability of the core 13 varies as shown in FIG. 10B due to its hysteresis property shown in FIG. 10A. In the figure, "n" is the number of turns of the coil, and "i" is a coil current. When a voltage waveform of an AC power of a waveform shown in FIG. 9A is shifted to a positive side by an influence of an external magnetic flux, as shown in FIG. 9B, a DC component is generated. However, a voltage waveform of the AC power of a waveform is shifted to a negative side by the influence of the external magnetic flux, as shown in FIG. 9C, a negative DC component is generated. If the external magnetic flux is alternate one, such shifts are repeated.

Accordingly an output voltage generated across the coil 14 varies as shown in FIG. 9D. As seen, under a condition that no external magnetic field is applied, a waveform of the voltage across the coil is symmetrical with respect to the zero level, and a positive peak value v1 of the voltage across the coil is equal to a negative peak value v2.

When the magnet 15 is made close to the coil 14 as indicated by a dotted line in FIG. 8, the magnetic flux passing through the core 13 is the sum of the flux generated by the coil 13 and the flux by the external magnetic field. Accordingly, a voltage generated across the coil 14 takes a waveform as shown in FIG. 9E and v1>v2.

This fact shows that an external magnetic field can indirectly be detected in a manner that the positive value V1 and negative value V2 of the voltage across the coil 14 are compared, and difference between them is obtained. If this is applied to the leakage flux flaw detecting method, a flaw can be detected because a leakage flux is generated by a flaw.

In the inventions based on the principle as mentioned above, a magnetic flux measurement is performed by supplying an AC power at predetermined frequency and voltage to a coil wound around a ferromagnetic core through a fixed impedance means, and by detecting a level of a DC component of a voltage generated across said coil.

When considering a waveform of the voltage generated across the coil 14 from another view, the times $\tau$ and $\tau_T$ during when voltage levels reach fixed reference voltages $E_R$ and $-E_R$ respectively become $\tau_T = 2\tau$, as shown in FIG. 11A, in a situation that no external magnetic field is applied. When external magnetic field is applied, the times $\tau$ and $\tau_T$ during when voltage levels reach fixed reference voltages $E_R$ and $-E_R$ respectively become $\tau_T \neq 2\tau$, as shown in FIG. 11C.

Accordingly, an external magnetic field can be measured in a manner that, as shown in FIGS. 11B and 11D, a waveform of the voltage generated across the coil is converted into a voltage signal of a fixed amplitude by a level discriminating circuit with reference voltages $E_R$ and $-E_R$, such as a comparator having a hysteresis characteristic:, and times $\tau_1$ and $\tau_2$ during when the voltage level change from $E_R$ to $-E_R$ and from $-E_R$ to $E_R$ respectively are measured in terms of a pulse width of the converted voltage signal, and the measurement results are used.

In another invention based on the above principle, for the magnetic flux measurement, a level discriminating circuit produces a voltage signal in accordance with a waveform of the voltage generated across the coil, and a pulse width of the voltage signal is detected.

In still another invention, the fixed impedance means is replaced with a second coil whose core is made of ferromagnetic material. The impedances of the two coils vary in response to an external magnetic field whose magnetic flux crosses the coils. A connection point between those coils provides a voltage proportional to a difference between the magnetic field intensities of the coils. Accordingly, a magnetic flux measurement is possible by appropriately processing the voltage by using a DC component detecting means and a pulse width modulating means.

Temperature variation influences the winding resistance of the coil and the permeability of the ferromagnetic core, although the influence is a little. A variation of the impedance of the coil due to the temperature variation causes the magnetizing current to equally vary in the positive and negative swings. Accordingly, the variations are canceled out to each other, causing no drift of the output voltage due to the temperature variation. When the magnetizing current flowing through the coil is increased till the ferromagnetic core is saturated, the output voltage across the coil is clipped at a fixed value. The positive and the negative amplitudes and the phase of the voltage across the coil are varied by only the magnitude of the external magnetic field. This indicates that the detection sensitivity is insensitive to the variations of the output voltage of the power source and the resistance of the fixed impedance means if the variations are within a tolerable range.

Another inventions improve a measuring span of the magnetic flux sensor. Where no flaw is contained in the test piece to be detected a leakage flux essentially occurs. In the inventions, the pulse current superposed by a DC bias component is fed to the magnetic flux sensor. If the leakage flux crosses the sensor, it can be canceled within the sensor.

Another invention may vary a DC bias voltage in accordance with a level of the leakage flux by varying the DC bias voltage applied to the sensor in accordance with a level of a DC component of the voltage across the coil.

In another invention, an AC magnetizing current having a predetermined RMS is applied from the magnetizing signal wave generator to the detection coil of the magnetic sensor. Since the RMS of this AC magnetizing current is larger than that of the pulse signal of a trigger waveform, the voltage of the AC magnetizing current required for magnetizing the core of the magnetic sensor can be set to be low.

The core is magnetized to the positive and negative directions by the AC voltage applied to the detection coil. The core is saturated when a current value exceeds a predetermined value. A waveform of a detection signal extracted across the detection coil is a waveform having a predetermined width. In a state wherein a detection signal having a predetermined width is output from a detection coil mounted on the core magnetized to the saturable range, when an external magnetic field is applied in a direction perpendicular to the magnetic field generated by the AC magnetizing current, the external magnetic field is added to or subtracted from the magnetic field generated by the AC magnetizing current, and the waveform of the detection signal is partially deformed. The deformed detection signal waveform is normalized with a predetermined threshold value in the waveshaper. A degree of deformation of the detection signal waveform is detected by a pulse width of the normalized signal. Therefore, the external magnetic field intensity can be detected in accordance with a change in this pulse width.

The means for obtaining a pulse width may be a means for directly measuring the pulse width by a counter or a means for measuring the pulse width by causing a low-pass filter to detect an average DC component of the normalized signal.

In another invention, positive and negative pulse voltages are applied from the pulse voltage supply source to a coil of a magnetic sensor located near the target magnetic field, positive and negative peak values of voltages generated across the coil are respectively detected by a pair of peak value detecting means, and the detected peak values are added by an adder, so that a change in target magnetic field (external magnetic field) detected by the magnetic sensor is detected as a change in voltage level.

In still another magnetic field measuring apparatus of the present invention, positive and negative pulse voltages are applied to coils of a plurality of magnetic sensors, voltages generated across the coils are sequentially and alternatively extracted by selecting means, the positive and negative peak values of the extracted voltages are respectively detected by a pair of peak value detecting means, and the detected peak values are added by an adder. Therefore, changes in target magnetic field (external magnetic field) detected by the respective magnetic sensors are output from the adder as voltage signals.

In still another magnetic field measuring apparatus according to the present invention, positive and negative pulse voltages are sequentially and alternatively applied to coils of a plurality of magnetic sensors, and voltages generated in synchronism with the application of the positive and negative pulse voltages are sequentially and alternatively extracted. Therefore, one pulse voltage is supplied to one coil each time, and power consumption is kept unchanged as compared with an arrangement having one magnetic sensor.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 shows an explanatory diagram for explaining a conventional leakage flux flaw detecting method;

FIG. 2 is a graph showing relationships between leakage flux density vs. distance between the surface of a steel material detected and a Hall device in FIG. 1;

FIG. 3 is a perspective view showing a steel material with a flaw used in FIG. 2;

FIG. 9A shows waveform of an output voltage of an oscillator in the circuit of FIG. 8;

FIG. 9B is a waveform chart showing a case wherein the waveform shown in FIG. 9A includes a positive DC component;

FIG. 9C is a waveform chart showing a case wherein the waveform shown in FIG. 9A has a negative DC component;

FIGS. 11A through 11D show waveforms of the voltages outputted from the oscillator and across the coil, which are useful in explaining an additional principle of the present invention;

FIG. 30 is a circuit diagram showing an additional embodiment of the present invention;

FIG. 31 is a block diagram showing still another embodiment of the present invention;

FIG. 32 is a graph for explaining an operation of the embodiment shown in FIG. 31;

FIG. 35 is a block diagram showing still another embodiment of the present invention;

FIG. 36 is a graph showing relative sensitivity characteristics of minute magnetic flux detection sensitivity upon a change in T/τ in the embodiment shown in FIG. 35;

FIG. 39 is a block diagram showing still another embodiment of the present invention;

FIGS. 40, 41 and 42 are block diagrams showing still another embodiments of the present invention, respectively, corresponding to the embodiment shown in FIG. 20;

FIGS. 43, 44, 45 and 46 are block diagrams showing still another embodiments of the present invention, respectively, corresponding to the embodiment shown in FIG. 28;

FIGS. 47, 48, 49, and 50 are block diagrams showing still another embodiments of the present invention, respectively, corresponding to the embodiment shown in FIG. 30; and FIGS. 51, 52, 53, 54, 55 and 56 are block diagrams showing still another embodiments of the present invention, respectively, corresponding to the embodiment shown in FIG. 31.

DETAILED DESCRIPTION OF THE PREFERRED EMBODIMENTS

There will now be described embodiments of the present invention with reference to the accompanying drawings.

Figure 12:
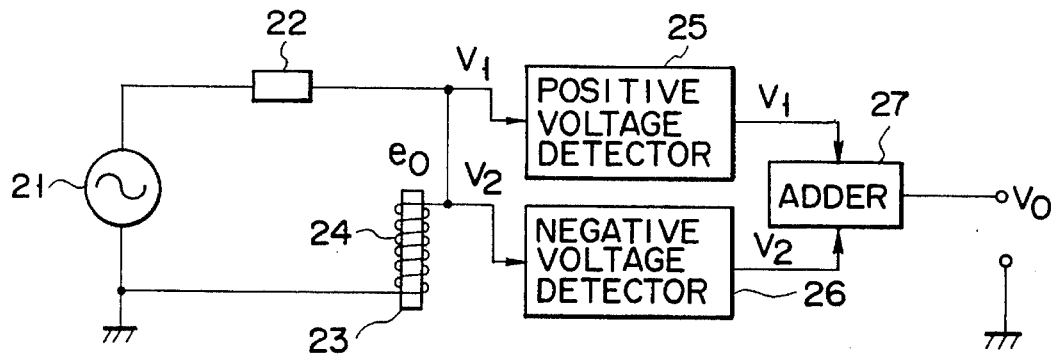
FIG. 12 is a circuit diagram showing an embodiment of the present invention.

As shown in FIG. 12, an oscillator 21 at predetermined frequency and voltage is coupled with a series connection circuit of a resistor 22 as a fixed impedance means and a coil wound around a ferromagnetic core 23. A voltage $e_o$ generated across the coil 24 is applied to a positive voltage detector 25 and a negative voltage detector 26. The output voltages of these detectors 25 and 26 are applied to an adder 27, which produces an output voltage Vo. In this embodiment, an AC current is fed from the oscillator 21 to core 23 through the resistor 22, till the core 23 is saturated.

The voltage across the coil 24 is detected by the detectors 25 and 26. The detector 25 produces a DC voltage V1 which is proportional to a positive voltage v1 of the voltage eo. The detector 26 produces a DC voltage V2 which is proportional to a positive voltage v2 of the voltage eo.

The DC voltages V1 and V2 are applied to the adder 27, where V1+(−V2) is calculated. The adder produces an output voltage Vo. Where no external magnetic field is applied to the core 23, |V1|=|V2| and hence the output voltage Vo is 0 V. Where an external magnetic field is applied to the core 23, the DC voltages V1 and V2 vary in accordance with the polarity and the intensity of the external magnetic field. Accordingly, the output voltage Vo of the adder 27, Vo=V1+(−V2), depends on the external magnetic field. Therefore, a minute magnetic flux coupled with the coil 24 can be measured in terms of the output voltage Vo. In a state wherein an external magnetic field is not generated, an output voltage is supposed to be set to be Vo=0. Even if an external magnetic field is not, however, generated, when asymmetry (waveform distortion) is present in a waveform of an output voltage (magnetizing voltage as of a triangular wave) from the oscillator 21 is present, the detection voltage Vo cannot be set to zero. A voltage detected even in the absence of the external magnetic field is defined as a bias voltage VB in FIG. 12.

Figure 13:
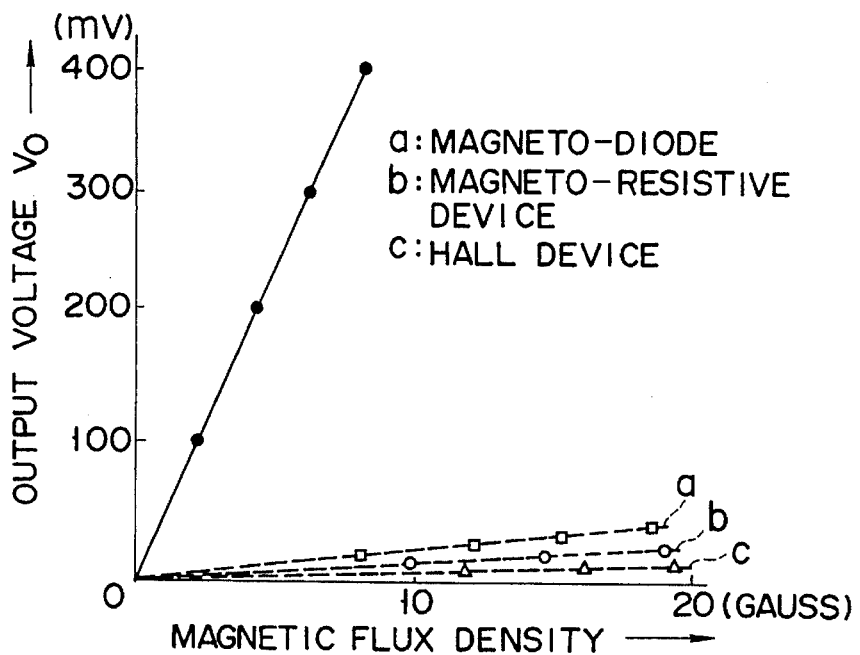
FIG. 13 is a graph showing a magnetic flux density vs. output voltage characteristic (detecting sensitivity characteristic) of the embodiment of FIG. 12.

The magnetic flux measuring system of the present embodiment was used and the result of the measurement is as shown in FIG. 13. For a minute magnetic flux variation of 0 to 10 gauss, the output voltage Vo varied in a broad range of 0 to about 500 mV. This shows remarkable improvement of the sensitivity. In FIG. 13, a line "a" indicates a sensitivity of a magneto-diode as a magnetic flux sensor; a line "b", that of a magneto-resistive device; a line "c", that of a Hall device. These a, b and c correspond to those of FIG. 2.

If this measuring system is applied to the leakage flux flaw detecting method for detecting flaws of a steel pipe, a steel plate and the like, the flaw detection can be made with a high precision.

Figure 14:
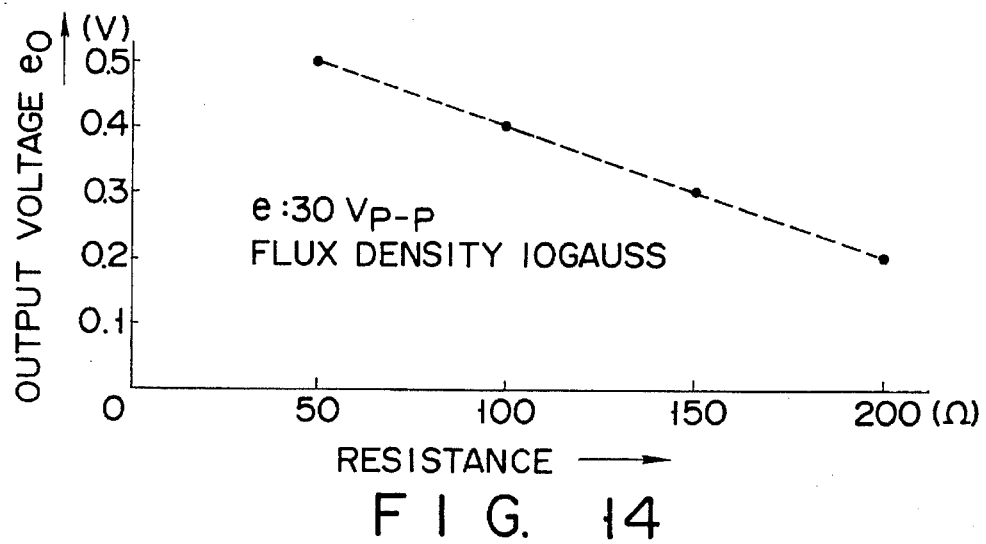
FIG. 14 is a graph showing a variation of a voltage across the coil against a resistance variation.

In another measurement of the measuring system of the present embodiment, the output voltage eo of the oscillator 21 was 30 Vpp (peak to peak voltage), the magnetic flux density was fixed at 10 gauss, and the resistance R1 of the resistor 22 was varied at 50, 100, 150, and 200 ohms. The output voltages eo obtained were plotted as shown in FIG. 14. While the resistance of the resistor 22 is changed 0 to four times, the output voltage eo varies about 0.5 V to 0.2 V. A sensitivity difference for the minute magnetic field intensity was approximately 60%. If a metal coated resistor is used for the resistor 22, its resistance change is 1% or less for temperature variation of 0 to 80° C. Practically, the detecting sensitivity is not changed by the temperature variation.

Figure 15:
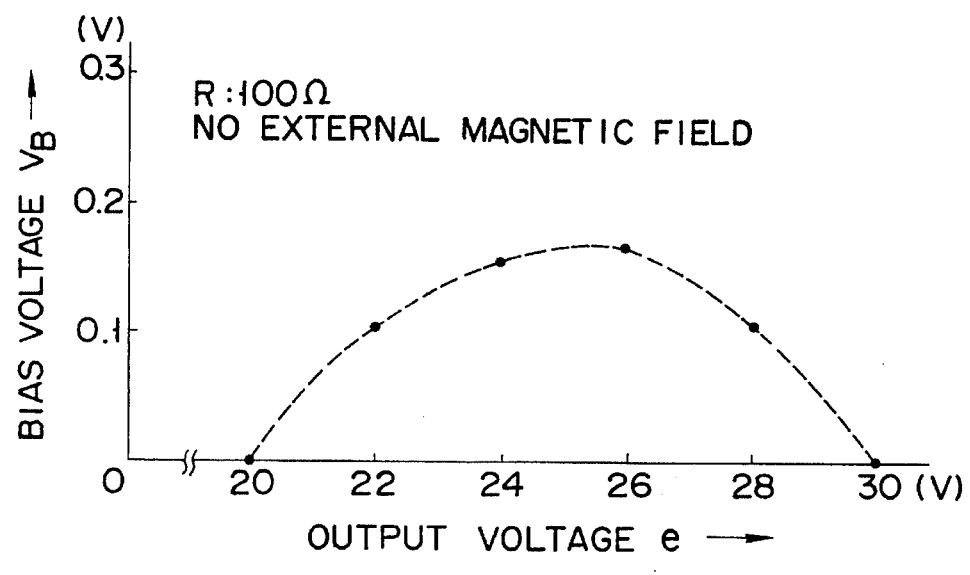
FIG. 15 is a graph showing a variation of a bias voltage of the coil against a variation of an output voltage of the oscillator.

A further measurement was conducted in a condition that resistance R1 of the resistor 22 was 100 ohms, and the output voltage eo of the oscillator 21 was varied between 20 and 30 Vpp. In the measurement, variation of a bias voltage VB of the coil 24 was measured and the result as shown in FIG. 15 was obtained. That is, a maximum of variation of the bias voltage VB was 0.17 V. When considering the fact that a variation of the output voltage eo of the oscillator 21 is usually below 1%, influence of the variation of the bias voltage upon the magnetic flux measurement can be negligible.

Figure 16:
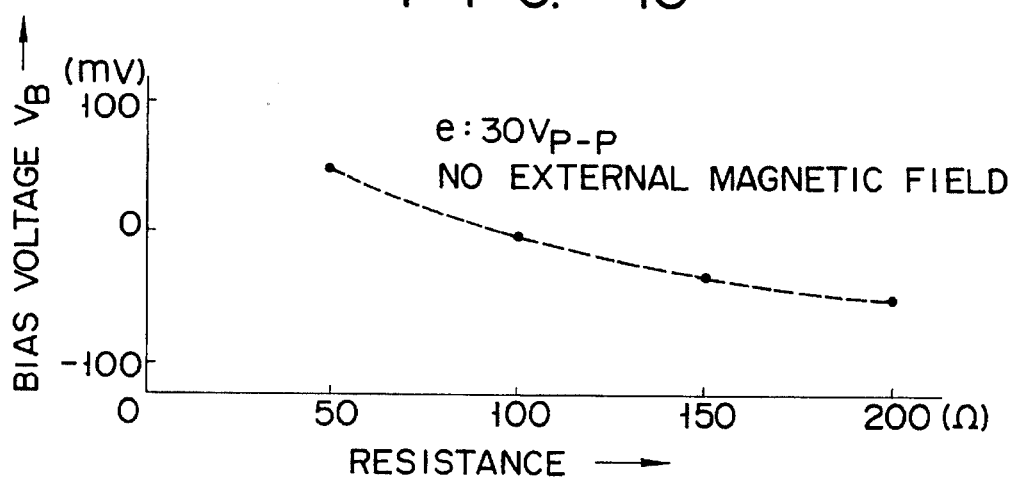
FIG. 16 is a graph showing a variation of a bias voltage of the coil against a resistance variation.

In an additional measurement, the output voltage of the oscillator 21 was set at 30 Vpp and the resistance R1 of the resistor 22 was changed to 50, 100, 150 and 200 ohms, and thus the bias voltage VB of the coil 24 was measured. The result of the measurement is shown in FIG. 16. The variation of the bias voltage VB was 0.1 v. Since the temperature variation of the practical resistor 22 is below 0.1%, a variation of the drift voltage against the temperature variation can be negligible.

Another embodiment of the present invention will be described with reference to the accompanying drawings. Like reference symbols are used for designating like portions in the previous embodiment.

Figure 17:
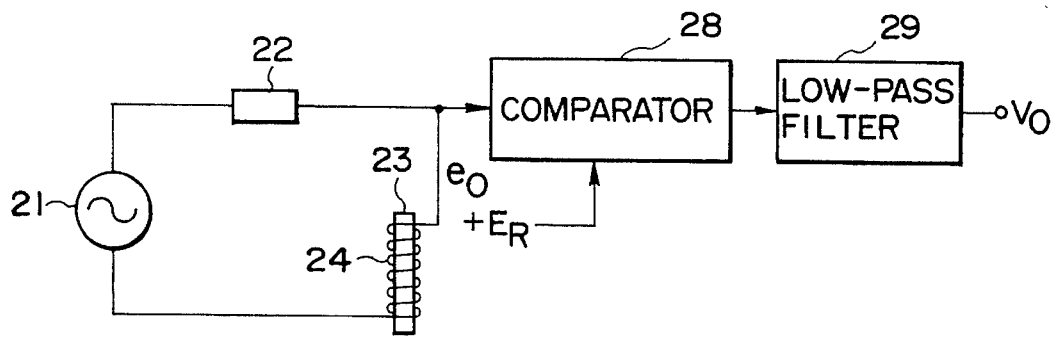
FIG. 17 is a circuit diagram showing another embodiment of the present invention.

In the second embodiment, as shown in FIG. 17, when an AC current of a predetermined frequency and a predetermined voltage is supplied from an oscillator 21 to a coil 24, an output voltage eo corresponding to this AC current is generated by the coil 24. When an external magnetic flux is applied in a direction which is not perpendicular to the coil (i.e., target magnetic field=0), the amplitude and waveform of a positive component in a voltage generated across the coil 24 are equal to those of a negative component. No change in voltage waveform in output voltage eo does not appear in correspondence with the external magnetic field, as a matter of course. On the other hand, when an external magnetic field (regardless of a DC or AC magnetic field) is applied in a direction perpendicular to the coil 24 (i.e., target magnetic field ≠0), a voltage corresponding to the external magnetic field is added to a voltage generated across the coil 24. For this reason, the amplitudes and waveforms of the positive and negative components of the output voltage eo are changed by a sum voltage in correspondence with the magnitude of the external magnetic field. In this manner, the output voltage eo is amplified into a predetermined value by a comparator 28 and the amplified voltage is filtered through an LPF (low-pass filter) 29 including a resistor and a capacitor. The AC voltage component is eliminated, and only the voltage Vo is detected. The voltage Vo corresponds to the magnitude of the external magnetic field applied in a direction perpendicular to the coil 24. Therefore, the magnitude of the external magnetic field can be detected by measuring the voltage Vo.

Figure 18:
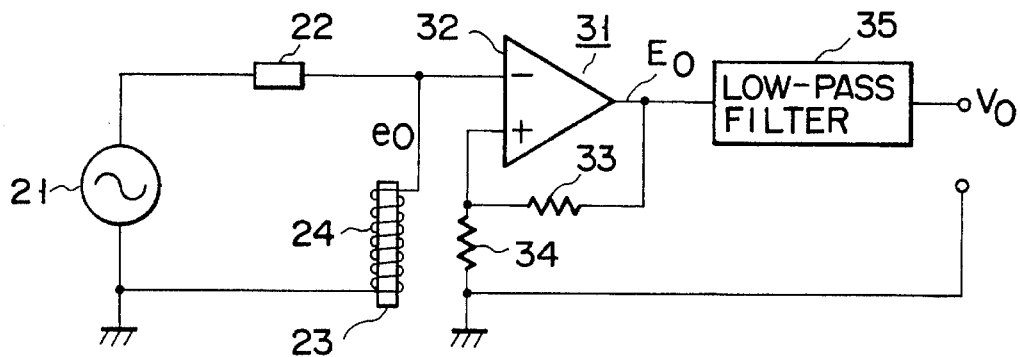
FIG. 18 is a circuit diagram showing yet another embodiment of the present invention.
Figure 19:
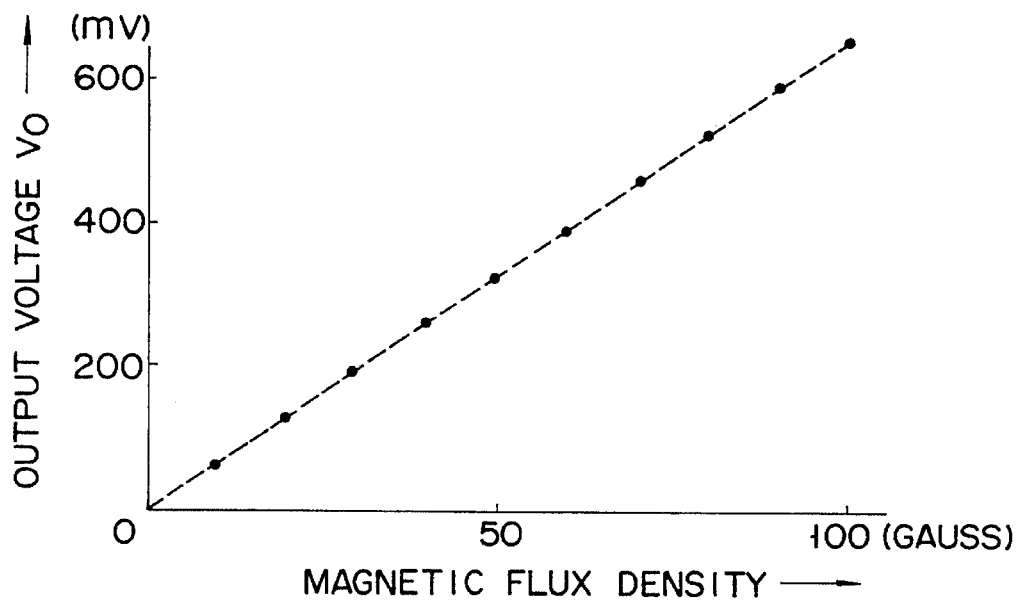
FIG. 19 is a graph showing a magnetic flux density vs. output voltage characteristic (detecting sensitivity characteristic) of the embodiment of FIG. 18.

A still another embodiment of the present invention will be described. As shown in FIG. 18, the output voltage eo across the coil 24 is applied to a comparator 31 as a level discriminating circuit. The comparator 31 is made up of an operational amplifier 32, and resistors 33 and 34. The voltage eo is applied to the inverting input terminal (−) of the amplifier 32. The resistor 33 is inserted between the output terminal and the non-inverting input terminal (+) of the operational amplifier 32. The resistor 34 is connected between the non-inverting input terminal (+) and the ground. The output signal of the comparator 31 is applied to a low-pass filter 35, and is outputted as an output voltage Vo.

In the present embodiment based on the pulse width modulation system, the output voltage eo across the coil 24 is applied to the inverting input terminal (−) of the amplifier 32. The output signal Eo of the amplifier 32 is divided by the resistors 33 and 34, and is positively fed back to the non-inverting input terminal (+) of the amplifier 32.

A ratio of the resistances R2 and R3 of the resistors 33 and 34 is selected so as to satisfy the following relation.

$$|ER| = |ER|$$
$$= |Eo| \times R3/(R2 + R3),$$

where $|ER|$=reference voltage $|EP|$=positive feedback voltage.

Since the output voltage of the comparator 31 is a positive and negative voltages, the reference voltages ER and −ER as shown in FIG. 11A or 11C are automatically applied to the non-inverting input terminal (+) of the amplifier 32. Accordingly, the comparator 31 has a hysteresis characteristic. With such a characteristic, the comparator 31 produces an output signal as shown in FIG. 11B or 11D when the external magnetic field is absent or present. The output voltage is the pulse width modulated voltage. The output voltage thus produced is passed through the low-pass filter 35, so that the DC output voltage Vo can be derived depending on a differential value $(\tau_1-\tau_2)$ of the plus widths $\tau_1$ $\tau_2$. Therefore, the minute magnetic flux leaked to the outside can be measured by the output voltage Vo.

By using the measuring apparatus as mentioned above, a high output voltage Vo of 0 to 600 mV or more was obtained for a minute magnetic flux density of 0 to 100 gauss. The measuring apparatus of the embodiment above showed remarkable improvement of the detecting sensitivity.

The same advantageous effects are obtained by the present embodiment as those of the previous embodiments.

Figure 20:
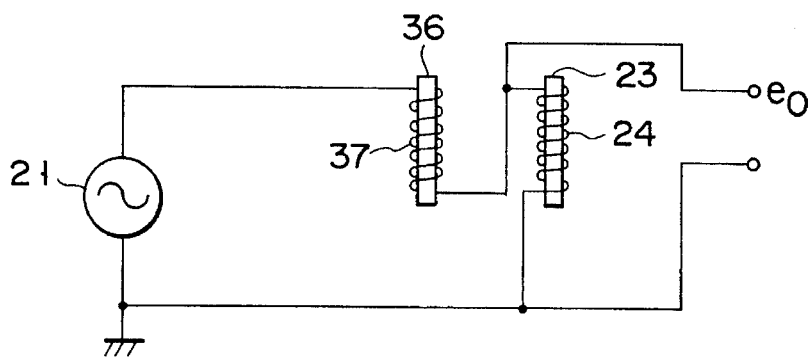
FIG. 20 is a circuit diagram showing still another embodiment of the present invention.

A further embodiment of the present invention is shown in FIG. 20. A coil 37 wound around a ferromagnetic core 36 is used as a second coil instead of the resistor 22 as a fixed impedance means. Assuming that the impedances of the coils 24 and 37 are Zs1 and Zs2 and the output voltage of the oscillator 21 is "e", the voltage eo across the coil 24 is $$eo=e.Zs2/(Zs1+Zs2).$$

The impedances Zs1 and Zs2 of those coils 24 and 37 vary in accordance with an external magnetic field coupling with them. Therefore, the output voltage eo is proportional to a difference between the intensities of the magnetic fields coupled with the coils 24 and 37.

As in the previous embodiments, if the output voltage eo is amplitude detected or pulse width modulated, only the difference of the magnetic field intensities can be measured. Thus, the minute magnetic flux can be measured at a high detecting sensitivity by the two coils wound around the ferromagnetic cores in place of the fixed impedance element.

As seen from the foregoing description, the present invention successfully provide a magnetic flux measuring method and apparatus for embodying the same which are highly sensitive to a minute magnetic field, but insensitive to temperature variation.

Figure 21:
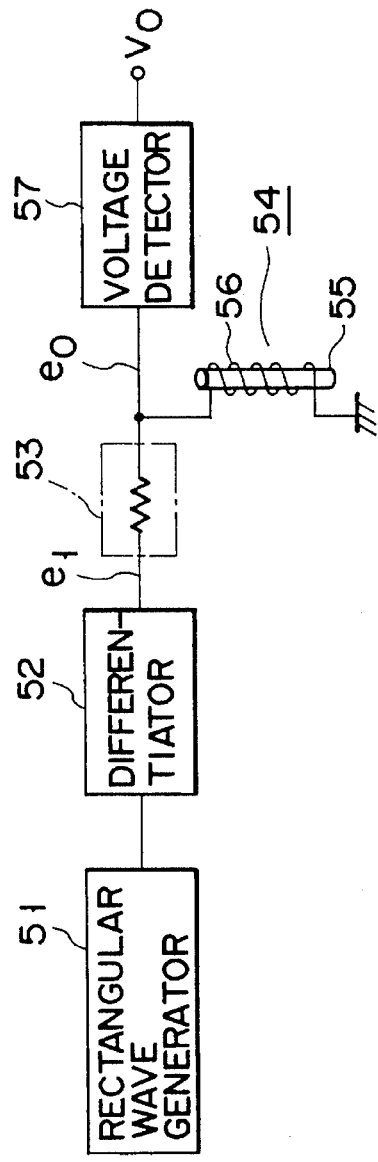
FIG. 21 is a circuit diagram showing still another embodiment of the present invention.

FIG. 21 is a block diagram showing a schematic arrangement of a minute magnetic flux detecting apparatus using a saturable magnetic sensor according to the present invention. Reference numeral 51 denotes a rectangular wave generator for generating an AC rectangular wave signal. A rectangular wave signal output from the rectangular wave generator 51 is converted into a pulse signal of a trigger waveform synchronized with leading and trailing edge timings of the rectangular wave by a differentiator 52 connected to the output of the rectangular wave generator 51. The pulse signal of the trigger waveform output from the differentiator 52 is supplied as an AC magnetizing signal e1 to a magnetic sensor 54 through an impedance element 53 comprising a resistor. The magnetic sensor 54 is arranged by winding a detection coil 56 on a ferromagnetic core 55 having, e.g., a rod-like shape. The AC magnetizing signal e1 is supplied to one terminal of the detection coil 56 of the magnetic sensor 54 through the impedance element 53, and the other terminal of the detection coil 56 is grounded. A terminal voltage of the detection coil 56 is extracted as a detection signal eo, and this signal is input to a voltage detector 57. The voltage detector 57 generates an output voltage Vo corresponding to the magnetic field intensity detected by the magnetic detecting apparatus.

In the minute magnetic flux detecting apparatus shown in FIG. 21, the voltage of the rectangular wave signal output from the rectangular wave generator 1 is controlled to increase a current of the AC magnetizing signal flowing through the detection coil 56, thereby magnetizing the core 55 up to a saturable range. In this state, therefore, the amplitude of the waveform of the detection signal eo representing the terminal voltage across the detection coil 56 becomes constant, as shown in FIG. 22.

Figure 22:
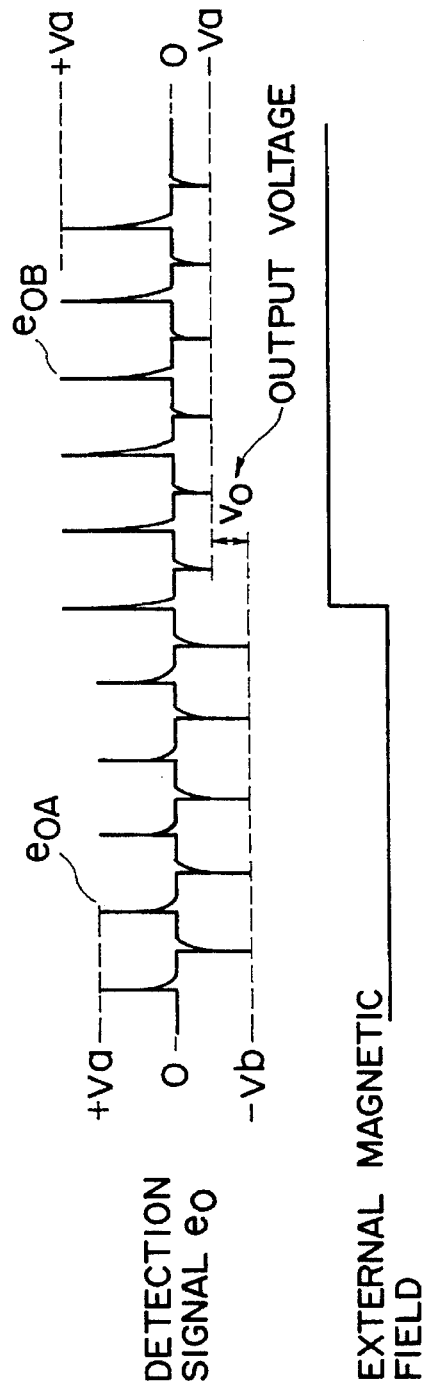
FIG. 22 is a timing chart for the invention shown in FIG. 21.

In a state wherein the external magnetic field is applied in a direction which is not perpendicular to the saturation magnetic field of the detection coil 6, the positive peak value Va of the waveform is equal to the negative peak value −Vb, as indicated by a left detection signal eoA in FIG. 22. However, when the external magnetic field comes close to the core 55 magnetized to the saturable range and crosses the saturation magnetic field generated by the detection coil 56, the amplitude value is not changed, but the positive and negative peak values Va and −Vb are changed, as indicated by a right detection signal eoB in FIG. 22. These peak values Va and −Vb are detected by a detector and are converted into DC components. The DC components are added to each other by an adder, thereby obtaining a difference voltage (Va−Vb). When the difference voltage (Va−Vb) is output from the voltage detector 57 as the output voltage Vo, this output voltage Vo corresponds to the external magnetic field applied to the magnetic sensor 54. Therefore, the magnetic field intensity can be detected by this magnetic field detecting apparatus.

In this manner, by using the saturable magnetic sensor, as compared with a magnetic field detecting apparatus utilizing a Hall element or a magneto-resistive element, the magnetic field detection sensitivity can be improved, and the measurement result is almost free from zero-point variations caused by changes in ambient temperatures, thereby improving measurement precision.

The above approach using the saturable magnetic flux sensor for the leakage flux flaw detecting method is advantageous in that the sensitivity for a weak magnetic field is excellent, but has the following problems.

Figure 23:
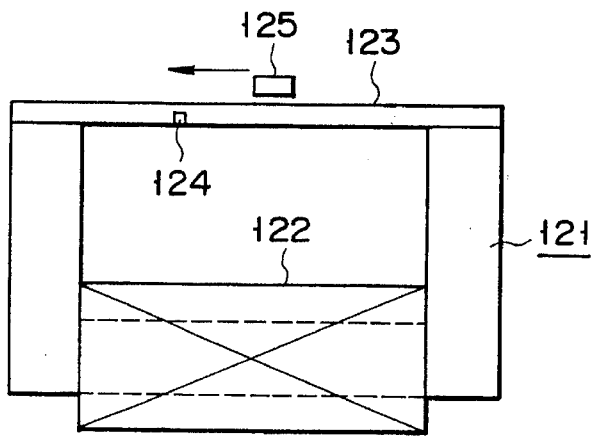
FIG. 23 shows an explanatory diagram for explaining a magnetic flux measuring apparatus.

As shown in FIG. 23, when a flaw detected piece 123 is magnetized by flowing a DC current to a coil 122 of an electromagnet 121, the piece provides a closed magnetic circuit for a magnetic field developed by the magnet 121. Accordingly, the magnetic flux passes mainly through the piece 123. Under this condition, if a magnetizing force (magnetizing current) is increased, the magnetic flux partially leaks to the outside of the piece 123. If a flaw 24 is present in the piece 123, a magnetic resistance at the flaw 124 increases, and thus the leakage flux thereat increases. Therefore, the flaw 124 can be detected by measuring a magnetic flux leaked from the flaw 124 by moving a saturable magnetic flux sensor 125 as set above the piece 123 in the direction of arrow.

Figure 24:
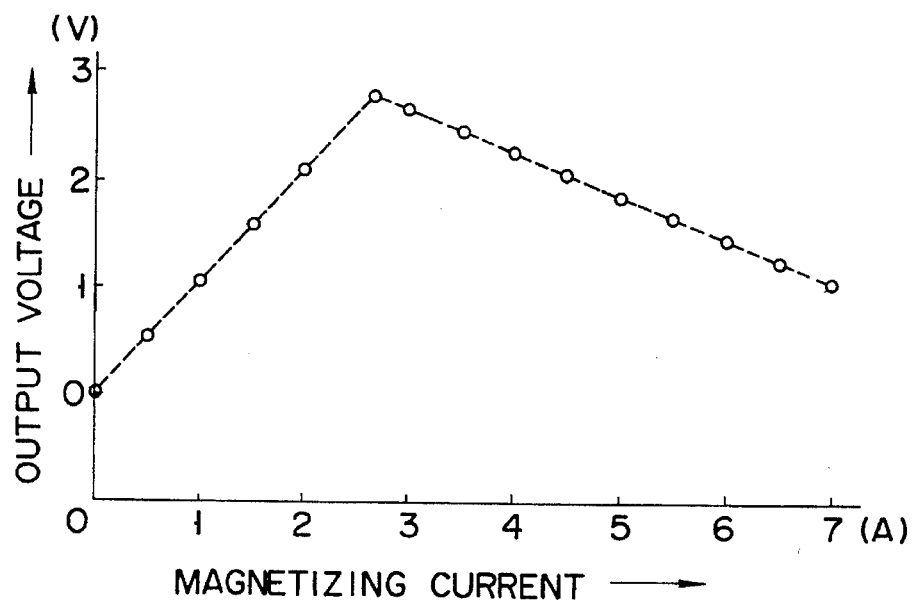
FIG. 24 is a graph showing a relationship of an output voltage vs. magnetizing current of the apparatus of FIG. 23.

A measurement was conducted in a condition that the sensor 125 shown in FIG. 23 was set above over the entire surface of the piece 123, and a magnetizing current of 0 to 7 A was fed to the coil 122 of the electromagnet 121. An output voltage of the flux sensor was measured. The result of the measurement was as shown in FIG. 24. The graph shows that the output voltage linearly increases in the range from 0 to 2.7 A of the magnetizing current, but when the magnetizing current exceeds almost 2.7 A, the output voltage is saturated and linearly decreases against the increase of the magnetizing current. As a result, the measuring span of the flux sensor is limited to be narrow. The narrow measuring span possibly degrades the flaw detection performance in the leakage flux flaw detection.

Another embodiment of the present invention provides a magnetic flux measuring method and apparatus for embodying the same which expand the measuring span of the magnetic flux sensor, and improves the flaw detection performance in the leakage flux flaw detection using the saturable magnetic flux sensor.

Figure 25:
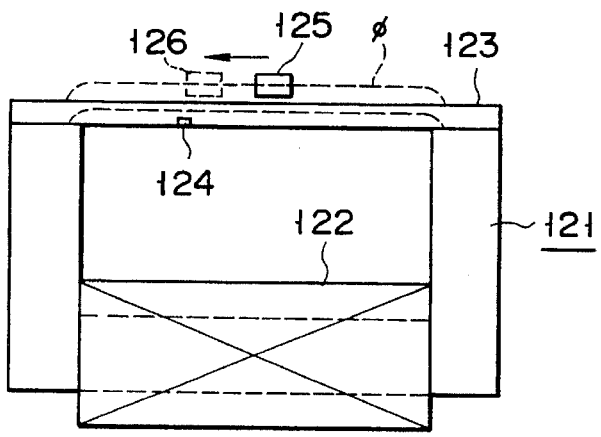
FIG. 25 is a diagram showing a diagram useful in explaining an additional principle of the present invention.

The principle of this embodiment will first be described. As shown in FIG. 25, if a DC current is fed to a coil 122 of a electromagnet 121 to magnetize a flaw detected piece 123, a magnetic flux partially leaks from the piece 123 even if the piece 123 has no flaw. The leakage flux $\phi$ thus links with a magnetic sensor 125, so that it produces an output voltage which varies as shown in FIG. 24 in response to the magnetizing current. Therefore, a magnet 126 for developing a local magnetic field is placed close to the magnetic sensor 125. The polarity of the local magnetic field is set to be opposite to that of a magnetic field developed by the coil 122. The intensity of the former is set to be equal to that of the latter. Under this condition, the output voltage of the magnetic flux sensor is 0 v. Accordingly, the measuring span of the magnetic flux sensor can apparently be expanded. In this instance, the function of the magnet 126 is realized by a DC bias voltage added to a pulse current from an oscillator.

Figure 26:
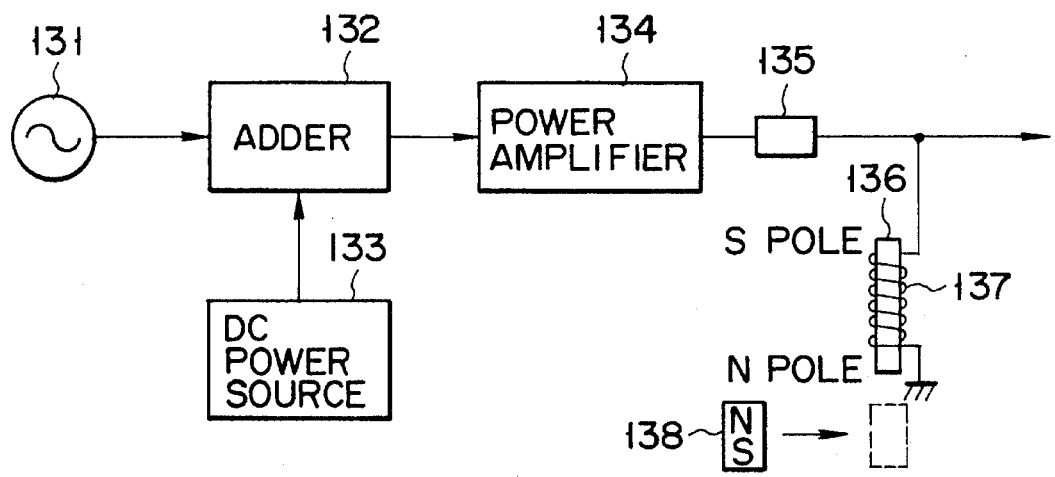
FIG. 26 is a block diagram showing a circuit of the apparatus of FIG. 25.

AS shown in FIG. 26, a high frequency voltage (pulse current) outputted from an oscillator 131 is applied to an adder 132. A DC power source 133 applies a DC bias voltage to the adder 132. The adder 132 adds together the high frequency voltage from the oscillator 131 and the DC bias voltage from the DC power source 133, and applies the composite signal to a power amplifier 134. The output signal of the power amplifier 134 is applies through a resistor 135 as a fixed impedance to a coil 137 wound around a ferromagnetic core 136 which constitutes a magnetic flux sensor.

With such an arrangement, when a DC current flows through the coil 137 of the magnetic flux sensor, a DC magnetic field H=NI (AT) which depends on the number of turns N of the coil is generated. It is assumed now that the upper side of the magnetic flux sensor is set to S pole. An external magnet 138 whose upper side is set to N pole, is moved in the direction of arrow so that the magnetic field by the external magnet 138 intersects the magnetic field by the coil 137. Then, the magnetic field by the magnet 138 mutually repels with that by the magnetic flux sensor, so that the magnetic flux in the magnetic flux sensor is canceled.

Figures 27A, 27B, 27C:
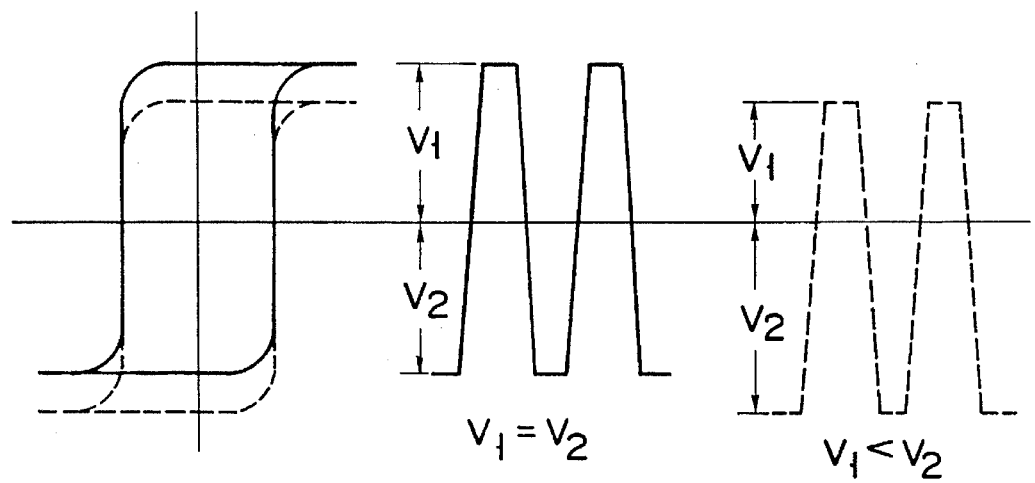
FIGS. 27A to 27C show waveforms showing a characteristic of the circuit of FIG. 26.

The supply of the DC current to the coil 137 of the magnetic flux sensor shifts a hysteresis curve of the core 136 of the magnetic flux sensor from a location indicated by a solid line to a location of a dotted line, viz., toward the negative side as shown in FIG. 27A. Accordingly, the output voltage characteristic of the magnetic flux sensor is changed from that shown in FIG. 27B to that shown in FIG. 27C. Thus, the use of the DC bias voltage shifts the characteristic of the magnetic flux sensor toward the negative side, and hence the operating point to the same.

An additional embodiment of the present invention will be described with reference to the accompanying drawings.

Figure 28:
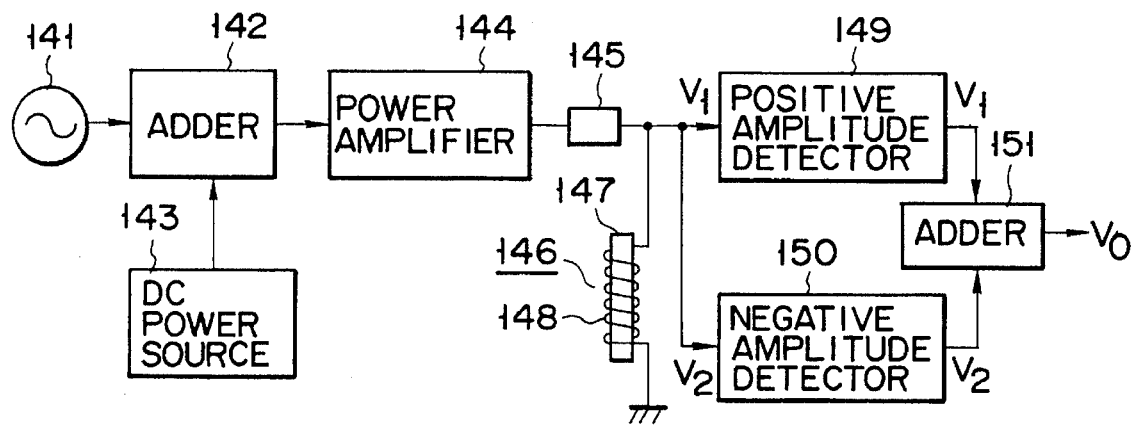
FIG. 28 is a circuit diagram showing another embodiment of the present invention.

As shown in FIG. 28, a high frequency voltage (pulse current) is supplied from an oscillator 141 to an adder 142. A DC power source 143 also applies a DC bias voltage to the adder 142. The adder 142 adds together the high frequency voltage from the oscillator 141 and the DC bias voltage from the DC power source 143, and supplies the composite signal to a power amplifier 144. The amplifier 144 amplifies the composite voltage signal and applies its output to a series connection circuit of a resistor 145 as a fixed impedance element and a coil 148 of the magnetic flux sensor 1.46, which is wound around a ferromagnetic core 147. An output voltage appearing across the coil 148 is applied to positive and negative amplitude detectors 149 and 150. The detected output signals of the detectors 149 and 150 are applied to an adder 151 where those are added together so as to output an output voltage Vo. The detectors 149 and 150, and the adder 151 make up a DC component detecting means.

With such an arrangement, the oscillator 141 applies a high frequency voltage to the adder 142. The DC power source 143 also applies a DC bias voltage to the adder 142. The adder 142 adds the high frequency voltage and the DC bias voltage together, and applies the resultant voltage to the power amplifier 144. The amplifier 144 appropriately amplifies the composite voltage signal and applies it through the resistor 145 to the magnetic flux sensor 146.

Consequently, an output voltage eo appears across the coil 148 of the magnetic flux sensor 146. The voltage eo is detected by the detectors 149 and 150. The positive amplitude detector 149 produces a DC voltage V1, which is proportional to a positive voltage v1 of the output voltage eo across the coil 148. The negative amplitude detector 150 produces a DC voltage V2, which is proportional to a positive voltage v2 of the output voltage eo across the coil 148. The DC voltages V1 and V2 are supplied to the adder 151 where V1+(−V2) is computed, and the result of the addition is outputted as an output voltage Vo.

Figure 29:
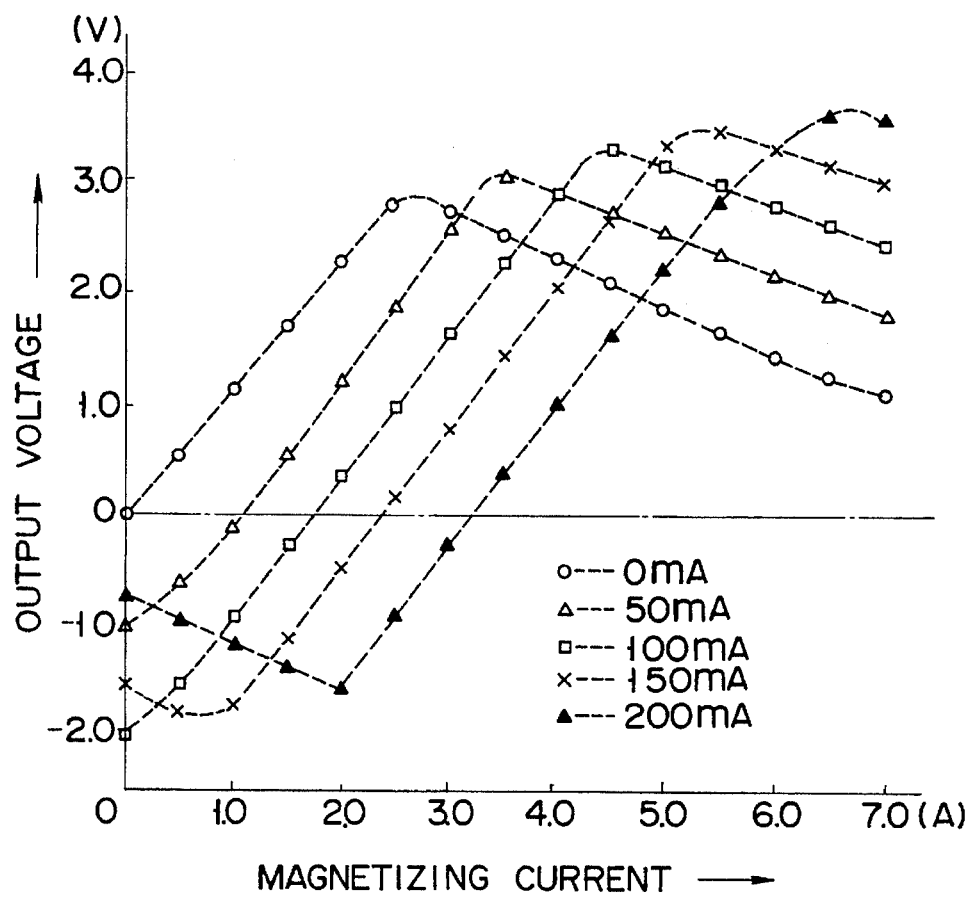
FIG. 29 is a graph showing a relationship of an output voltage vs. magnetizing current of the circuit of FIG. 28.

In a measurement by the measuring apparatus of this instance, a DC bias current from the DC power source 143 was changed to 0, 50, 100, 150, and 200 mA, and the output voltage of the magnetic flux sensor 146 was measured for those magnetizing currents. The results of the measurement were as shown in FIG. 29. As seen from the graph, when the DC current of 100 mA is supplied to the magnetic flux sensor 146, a linear characteristic of the output voltage of the magnetic flux sensor can be obtained in the range 0 to almost 4.5 A of the magnetizing current in companion with the DC current of 0 mA and thus a two times measuring span can be realized. Accordingly, the measuring span clan be broadened, improving the flaw detecting performance. When the DC current is further increased in excess of 100 mA, a measuring area to measure an intensity of the magnetic field is shifted while the measuring span remains unchanged.

An additional embodiment of the present invention will be described with reference to the accompanying drawings. Like reference symbols are used for designating like portions in the previous embodiment.

As shown in FIG. 30, a DC power source 143a, which can vary a variable DC bias outputted as a DC power source is provided. An output voltage Vo of the adder 151 is applied through a low-pass filter 152 to a differential amplifier 153. The differential amplifier 153 compares the output voltage received with a reference voltage derived from a reference voltage generator 154, and applies the difference voltage to the DC power source 143a. The power source 143a varies the DC bias in accordance with the voltage from the differential amplifier 153. The low-pass filter 152, the differential amplifier 153, and the reference voltage generator 154 constitute a control means for varying the DC bias.

With such an arrangement as shown in FIG. 30, even if the magnetizing current of the electromagnet, for example, is fixed, the leakage flux from the no flaw surface of the piece varies when a contact condition of the electromagnet with the detected piece, the thickness of the piece and the like are changed. The flaw detecting precision is improved by placing automatically the operating point at the center, for example, of the measuring span of the magnetic flux sensor 146.

In the arrangement of FIG. 30, an operating point of the magnetic sensor 146 is detected by the output voltage of the adder 151. A difference voltage between the output voltage and the reference voltage of the reference voltage generator 154 is obtained by the differential amplifier 153. The DC bias from the DC power source 143a is controlled by the difference voltage so that the output voltage Vo of the adder 151 when no flaw is contained in the piece is automatically compensated at 0 V. Accordingly, even if the measuring conditions change, a satisfactory measuring span is always secured, further improving the flaw detecting performance.

As seen from the foregoing, in the leakage flux flaw detection using the saturable magnetic flux sensor, the present embodiment is capable of expanding the measuring span of the magnetic flux sensor, thereby improving the flaw detecting performance.

FIG. 31 is a block diagram showing still another embodiment of the present invention. In this embodiment, an external magnetic field $\phi s$ is an AC external magnetic field, and a feedback circuit 160 is connected between the output terminal and one input terminal of an adder 142. An AC voltage generated by the AC external magnetic flux is measured. Negative feedback is performed on the basis of the measurement value, thereby adding a feedback component to the input to the feedback circuit 160. More specifically, when a feedback voltage Vn corresponding to the output voltage Vo is negatively fed back to the coil 148, the following output voltage Vo is obtained when a gain of the detector is defined as G. The feedback voltage Vn may be an AC or DC voltage:

$Vo=(Vs-Vn).G=(Vs-Vo.\beta).G$ $\therefore Vo=Vs.G/(1+\beta.G)$ where $\beta$ is the feedback constant.

Since $G \gg 1$, then $Vo=Vs/\beta$.

Since $Vs=m.\phi s$, then $Vo=k.\phi s$ ($k=m/\beta$: proportional constant)

Therefore, when the feedback constant $\beta$ is controlled in the feedback circuit 160, the measurement range of the external magnetic flux $\phi s$ can be arbitrarily adjusted. As shown in FIG. 32, the measurement range is the narrowest when the feedback circuit 160 is OFF. When the feedback constant $\beta$ is gradually increased in an order of $\beta 1 < \beta 2 < \beta 3 \ldots$, the measurable range for the external magnetic flux $\phi s$ is increased. According to this embodiment shown in FIG. 31, the external magnetic flux $\phi s$ which is large at the constant voltage Vo can be measured.

The minute magnetic flux measuring apparatus using the saturable magnetic sensor has been described in FIG. 21. However, the following problem is posed by even the minute magnetic flux detecting apparatus shown in FIG. 21. That is, a high-frequency magnetizing current is supplied to the detection coil 56 of the magnetic sensor 54 to magnetize the core 55 to a saturable range. In order to highly accurately detect the positive and negative peak values Va and −Vb of the detection signal eo extracted from the magnetic sensor 54, the high-frequency magnetizing signal e1 applied to the magnetic sensor 54 through the impedance element 53 is given as a pulse signal of a trigger waveform. The current flowing through the detection coil 56 becomes a high-frequency current due to the trigger waveform. In order to magnetize the core 55 to the saturable range by using the pulse signal of this trigger waveform, the voltage of the high-frequency magnetizing signal e1 must be greatly increased. For example, the voltage required in the compact magnetic sensor 54 is 15 to 25 $V_{P-P}$. In the rectangular wave generator 51, since a rectangular wave signal having a peak value of 15 to 25 $V_{P-P}$ must be output, a DC power source for a high voltage of 15 to 25 V must be used in addition to a DC power source of 5 V used in a conventional TTL circuit.

The voltage detecting apparatus 157 for calculating the output voltage Vo corresponding to the external magnetic field applied by the waveform of the detection signal eo includes a detection circuit for detecting positive and negative peak values Va and −Vb, an adder for adding the peak values Va and −Vb, and the like. Therefore, the circuit arrangement is undesirably complicated.

As described above, since a high-voltage DC power source, a detection circuit, an adder, and the like are required, the circuit arrangement of the magnetic field detecting apparatus as a whole is not only complicated but also bulky as a whole.

Figure 33:
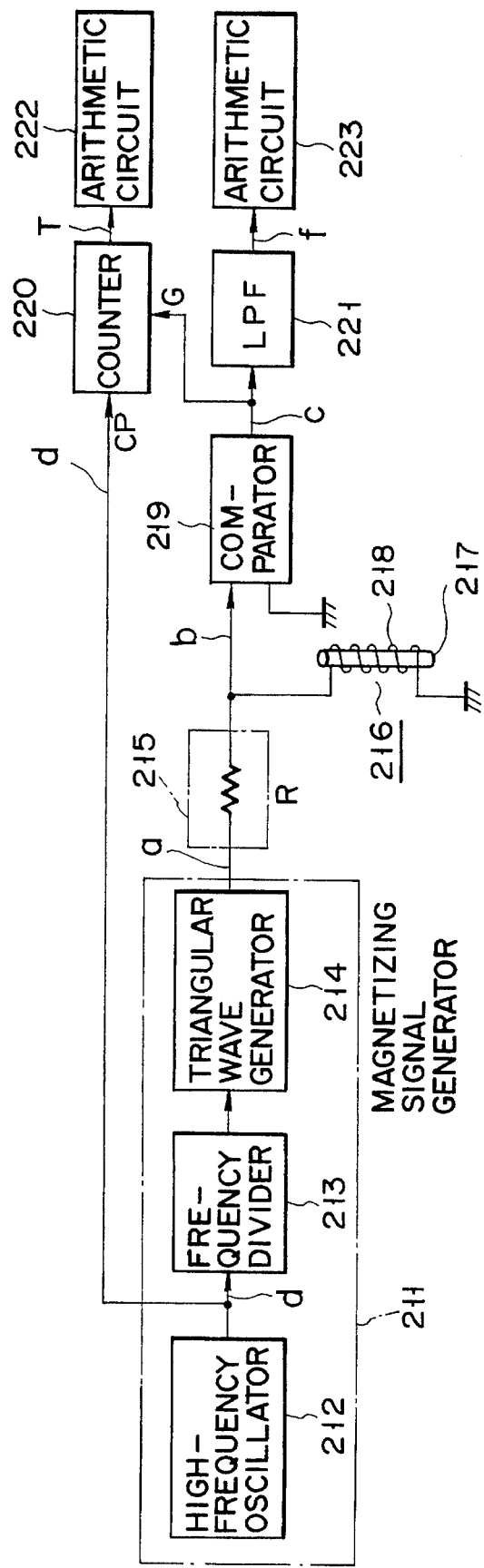
FIG. 33 is a block diagram showing still another embodiment of the present invention.

FIG. 33 is a block diagram showing a schematic arrangement of a magnetic field detecting apparatus according to still another embodiment of the present invention. Referring to FIG. 33, reference numeral 211 denotes a magnetizing signal generator for outputting a high-frequency magnetizing signal of, e.g., a triangular waveform as an AC magnetizing signal having a predetermined RMS. The magnetizing signal generator 211 comprises a high-frequency oscillator 212, a frequency divider 213, and a triangular wave generator 214. The high-frequency oscillator 212 generates a clock signal d having a high frequency of, e.g., 10 MHz. This clock signal d is frequency-divided into 1/N by the next frequency divider 213, and the frequency-divided component is input to the triangular wave generator 214. The triangular wave generator 214 sends a high-frequency magnetizing signal a as the AC magnetizing signal having a triangular waveform of a period T0, as shown in FIG. 34, to a magnetic sensor 216 through an impedance element 215 constituted by, e.g., a resistor.

Figure 34:
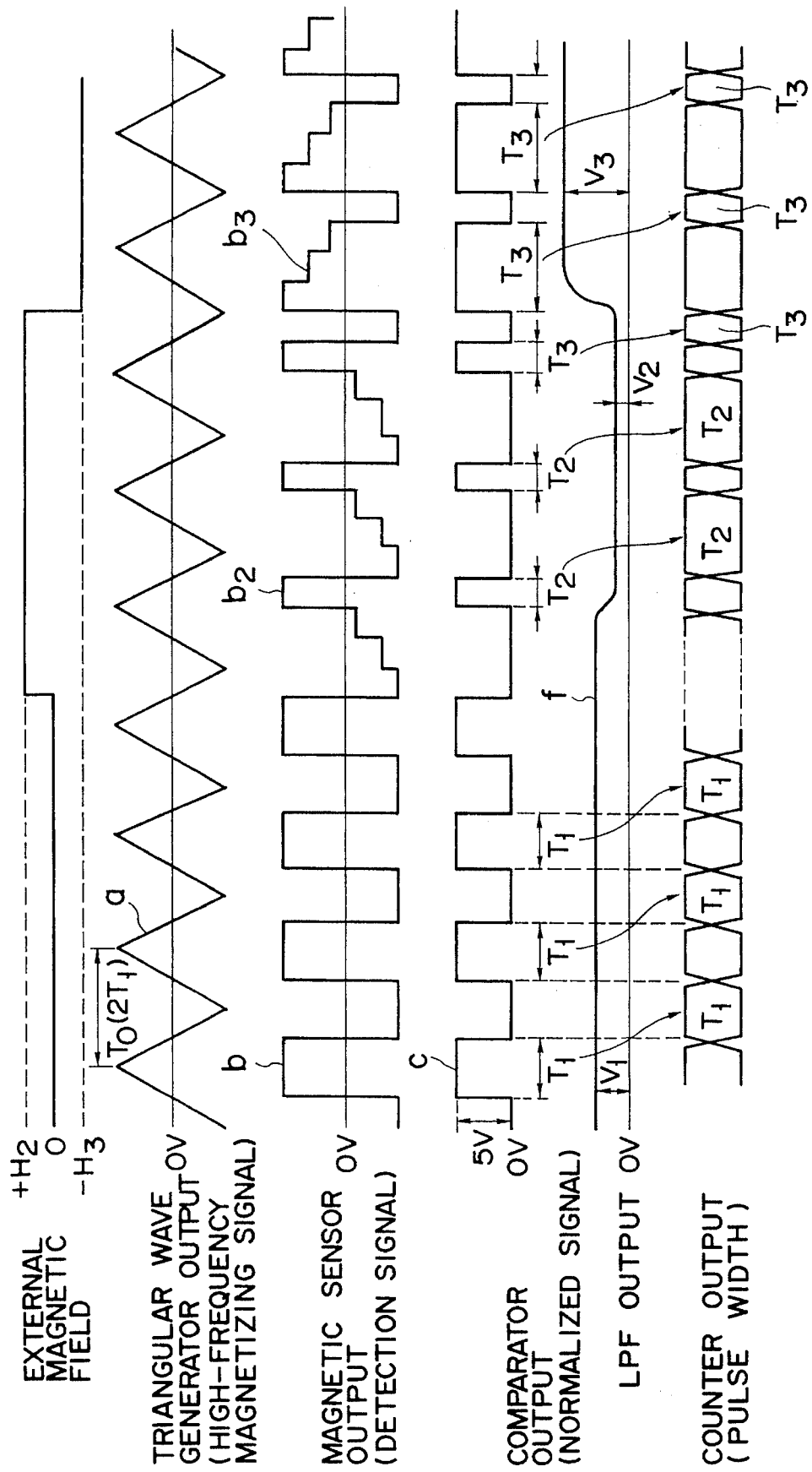
FIG. 34 is a timing chart for explaining an operation of the embodiment shown in FIG. 33.

As shown in FIG. 34, the magnetic sensor 216 is formed by winding a detection coil 218 around a ferromagnetic core 217 having, e.g., a rod-like shape. The high-frequency magnetizing signal a is applied to one terminal of the detection coil 218 of the magnetic sensor 216 through the impedance element 215, and the other terminal of the detection coil 218 is grounded. A terminal voltage across the detection coil 218 is extracted as a detection signal b of the magnetic sensor 216, and this detection signal is input to the noninverting (+) input terminal of a comparator 219 serving as a waveshaper. The inverting (−) input terminal of the comparator 219 is grounded. The detection signal b has a voltage higher than the ground potential (0 V), the comparator 219 is set at H (high) level. However, when the detection signal b is lower than the ground potential (0 V), the comparator 219 outputs a normalized signal c. The voltage level of the normalized signal c is 5 V as an H-level voltage and 0 V as an L-level voltage.

The normalized signal c having a predetermined level and output from the comparator 219 is input to a control terminal G of a counter 220 and to a low-pass filter 221. The clock signal d output from the high-frequency oscillator 212 is input to a clock terminal CP of the counter 220. The counter 220 starts counting clocks of the clock signal d in synchronism with a change in timing from L level to H level of the normalized signal c applied to the control terminal G. The counter 220 stops counting the clocks in synchronism with a change in timing from H level to L level of the normalized signal c. That is, the counter 220 counts a pulse width T represented by the H-level duration of the normalized signal c. The digital pulse width T measured by this counter 220 is supplied to an arithmetic circuit 222 constituted by, e.g., a microcomputer.

On the other hand, the low-pass filter 221 has a relatively large time constant and cuts off a high-frequency component of all the frequency components included in a pulse waveform of the normalized signal c, so that only a low-frequency component can pass through it. The low-pass filter 221 outputs an average DC voltage proportional to an RMS voltage of the normalized signal c. Since the average DC voltage of the normalized signal c corresponds to the pulse width T of the normalized signal c, a voltage of an analog output signal f from the low-pass filter 221 corresponds to the pulse width T of the normalized signal c. The output signal f having a voltage value corresponding to the pulse width T is input to an analog arithmetic circuit 223.

An operation of the magnetic field detecting apparatus having the above arrangement will be described below.

When a resistance of the impedance element 215 is defined as R and an impedance of the detection coil 218 of the magnetic sensor 216 is defined as Zs, the detection signal b extracted across the detection coil 218 satisfies the following equation for the high-frequency magnetizing signal a having a rectangular waveform and output from the magnetizing signal generator 211:

$$b=a \cdot Zs/(R+Zs)$$

In the above equation, since the resistance R is kept constant, the detection signal b is changed in accordance with a change in impedance Zs of the detection coil 218. The impedance Zs of the detection coil 218 wound around the ferromagnetic core 217 is proportional to a magnetic permeability $\mu$.

Figure 4:
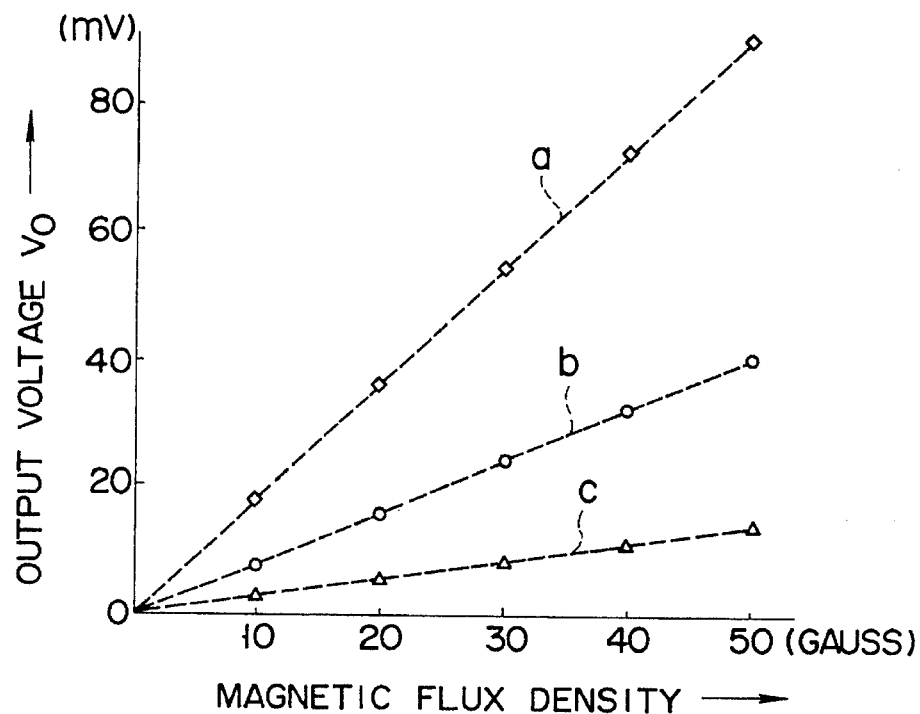
FIG. 4 is a graph showing relationships between, magnetic flux density and an output voltage of the various conventional sensor.
Figure 5:
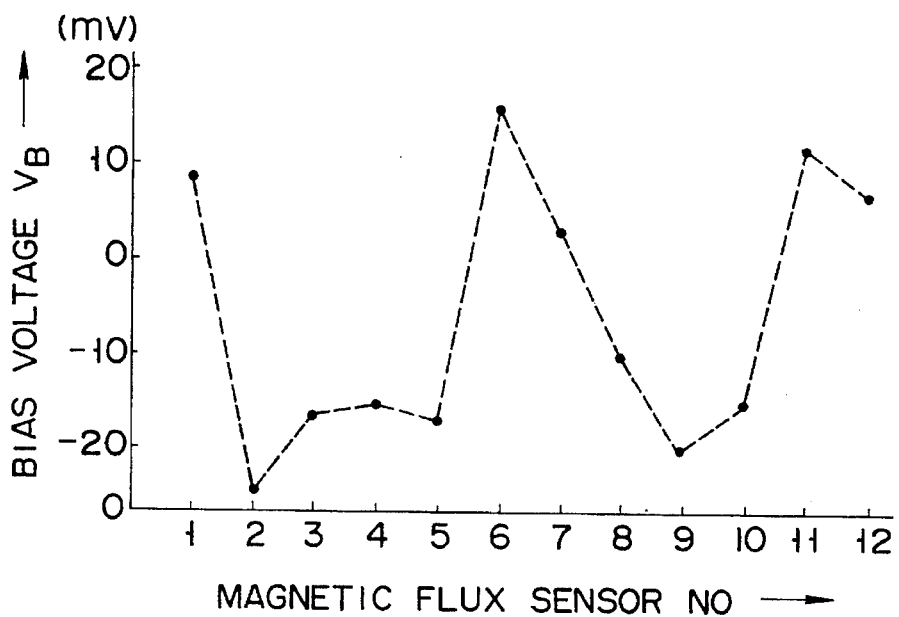
FIG. 5 is a graph showing a variation of initial bias voltages of magneto-resistive devices.
Figure 6:
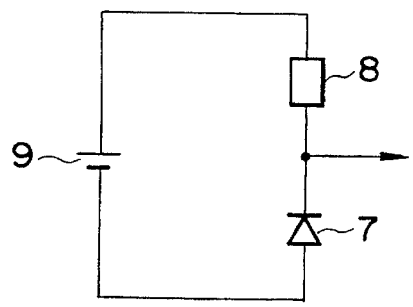
FIG. 6 is a circuit diagram showing a measuring circuit for measuring an output voltage vs. temperature characteristic of a conventional magneto-diode.
Figure 7:
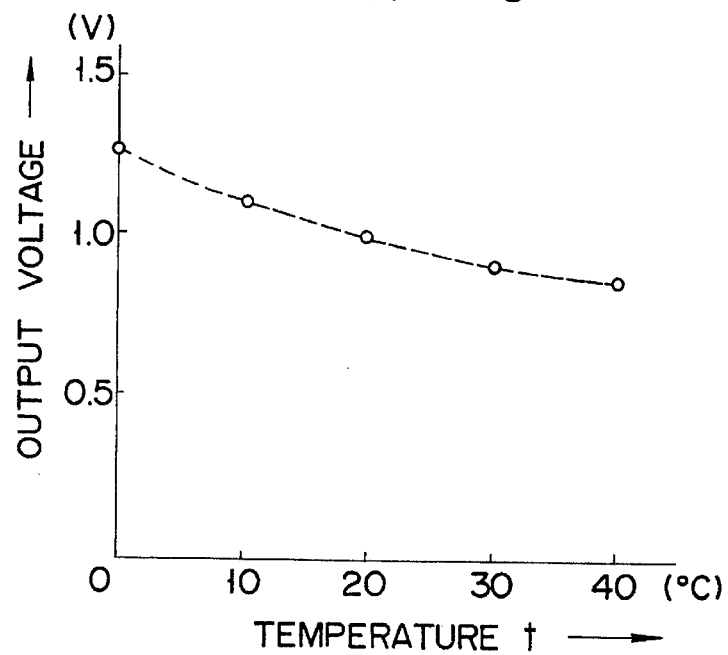
FIG. 7 is a graph showing an output voltage vs. temperature characteristic of the conventional magnetodiode as measured by using the circuit of FIG. 6.
Figure 8:
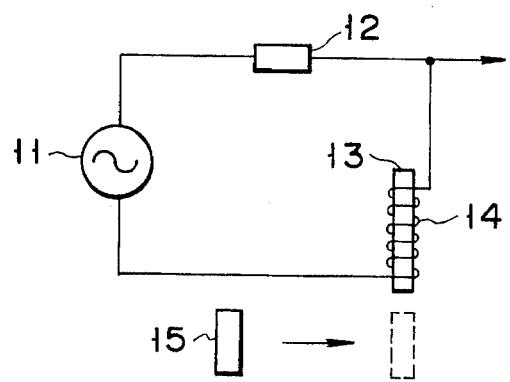
FIG. 8 is a circuit diagram for explaining the principles of the present invention.
Figure 9D:
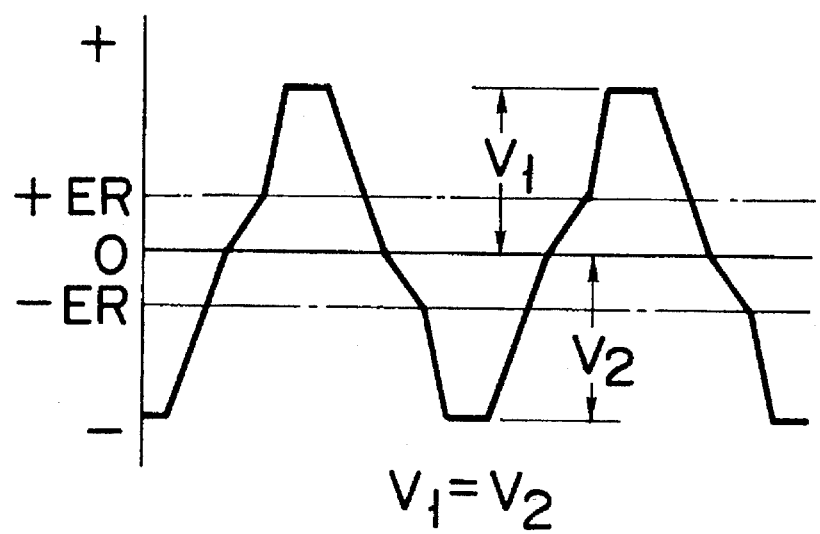
FIGS. 9D and 9E show waveforms of the voltages across a coil in the circuit of FIG. 8.
Figure 9E:
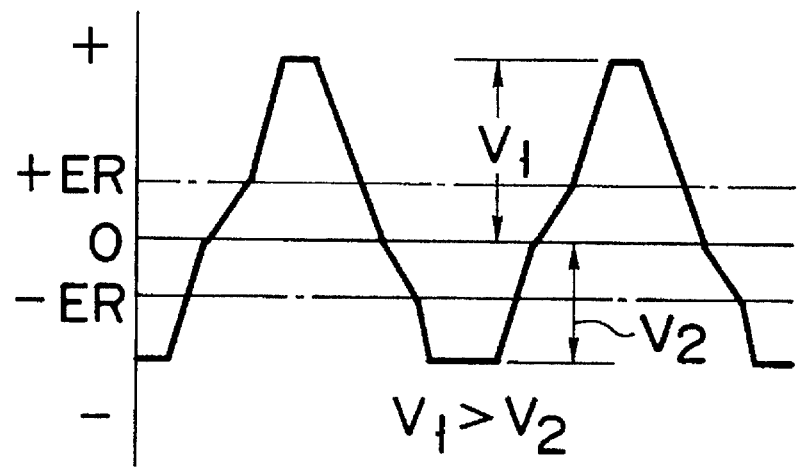
Figure 10A:
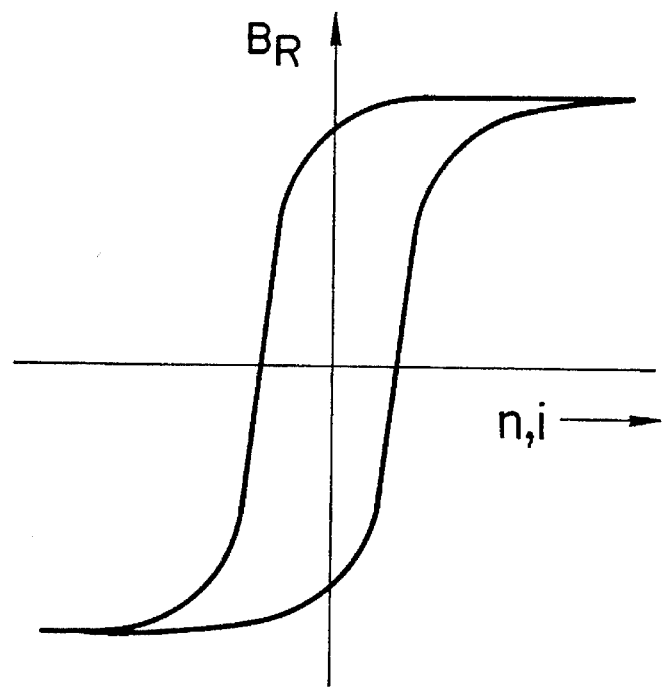
FIGS. 10A and 10B show a hysteresis characteristic and a magnetic permeability characteristic of a ferromagnetic core used in FIG. 8.
Figure 10B:
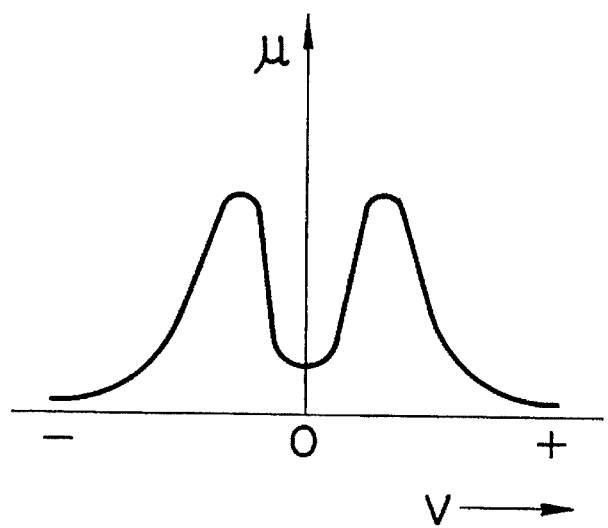

On the other hand, in the core 217 consisting of a ferromagnetic material, even if a magnetizing current is increased exceeding a predetermined value, an intensity of a magnetic field generated by this current is not increased exceeding a predetermined value, so that this generated magnetic field is saturated, as shown in FIG. 10A. In general, as shown in FIG. 10A, the magnetic field has a hysteresis characteristic. As shown in FIG. 10B, the magnetic permeability $\mu$ is also changed in accordance with a change in magnetizing current value. As a result, the impedance Zs of the detection coil 218 is also changed in accordance with a change in magnetizing current value, i.e., a value of the high-frequency magnetizing signal a applied to the detection coil 218. With an increase in the high-frequency magnetizing signal a shown in FIG. 34, the impedance Zs is abruptly changed, and the detection signal b is abruptly increased or decreased accordingly. The waveform of the detection signal b is an almost rectangular waveform extending to the positive and negative sides centered on 0 V, as shown in FIG. 34. A pulse width T1 of this rectangular waveform is ½ the period T0 of the high-frequency magnetizing signal a.

When the detection signal b having an almost rectangular waveform is input to the comparator 219, since the threshold value of the comparator 219 is 0 V, the normalized signal c output from the comparator 219 has the same pulse width T1 as that of the detection signal b. This pulse width T1 is measured by the counter 220 and is output to the arithmetic circuit 222. The arithmetic circuit 222 compares the input pulse width T1 with the known period T0 of the high-frequency magnetizing signal a. If T0=2T1, then the arithmetic circuit 222 determines that no external magnetic field is present.

The output signal f having the DC voltage V1 and output from the low-pass filter 221 is input to an arithmetic circuit 223. The arithmetic circuit 223 determines from the DC voltage V1 that no external magnetic field is applied.

In this state, when an external magnetic field H2 or −H3 having, e.g., an S or N pole crosses a magnetic field generated by the high-frequency magnetizing current, the external magnetic field H2 or −H3 is added to or subtracted from the magnetic field generated by the high-frequency magnetizing current, thereby changing the magnetic permeability $\mu$ of the core 217. The impedance Zs of the detection coil 218 is largely changed. Therefore, the waveform of the detection signal b of the magnetic sensor 216 is changed as indicated by a central detection signal b2 or a right detection signal b3 in FIG. 34.

The pulse width T of the normalized signal c output from the comparator 219 is changed from T2 to T3. The pulse width T input from the counter 220 to the arithmetic circuit 222 is changed from T1 to T2 or T3. The arithmetic circuit 222 calculates the applied external magnetic field H2 or −H3 in accordance with the pulse width T1 (=T0/2) and the resultant pulse width T1 or T2 in a state wherein any external magnetic field is not applied.

The pulse width T2 or T3 corresponding to the external magnetic field H2 or −H3 of the normalized signal c output from the comparator 219 is detected by the DC voltage V2 or V3 of the output signal f input from the low-pass filter 221 to the arithmetic circuit 223. In this analog arithmetic circuit 223, the applied external magnetic field H2 or −H3 is calculated in comparison between the pulse width and the DC voltage V1 in a state wherein no external magnetic field is applied.

As described above, the magnitude and direction of the external magnetic field applied to this magnetic field detecting apparatus can be calculated by the arithmetic circuits 222 and 223 as digital or analog values.

In the magnetic field detecting apparatus having the above arrangement, the waveform of the high-frequency magnetizing signal a as the AC magnetizing current applied to the magnetic sensor 216 is a rectangular waveform having a predetermined RMS, as shown in FIG. 34. The RMS of the high-frequency magnetizing signal a is larger than that of the pulse signal e1 of a trigger waveform in the detecting apparatus shown in FIG. 21. For this reason, the voltage of the high-frequency magnetizing signal a required to magnetize the core 217 of the magnetic sensor 216 to a saturable range can be set to be low. In the apparatus of this embodiment, a voltage value of the high-frequency magnetizing signal a can be reduced to 5 $V_{P-P}$. A DC power source for driving the high-frequency oscillator 212, the frequency divider 213, and the triangular wave generator 214 in the magnetizing signal generator 211 can generate a normal constant voltage of 5 V. That is, a DC voltage of 15 to 25 V is not required, unlike in the conventional apparatus. As a result, the circuit arrangement of the apparatus as a whole can be simplified.

A circuit for detecting an intensity of an external magnetic field from the detection signal b of the magnetic sensor 216 can be realized by simple, inexpensive circuit components such as a waveshaper constituted by the counter 220, the low-pass filter 221, and the comparator 219 having a relatively simple circuit arrangement. Therefore, the magnetizing signal generator 211, and detection signal processing circuits 219, 200, and 221 can be made compact, so that a compact, lightweight, and low-cost magnetic field detecting apparatus can be obtained.

Since the above circuits can be realized by TTL circuits, they can be formed into an IC, so that the apparatus as a whole can be further made compact.

Since an output signal from the counter 220 is a digital signal having a predetermined level, it is almost free from an influence of external noise. In addition, since the circuit arrangement is simple, inspection and repairing can be facilitated. Therefore, sufficient measurement precision can be obtained under severe conditions in production lines in factories.

When the comparator 219 is used as the waveshaper as in the above embodiment, the arrangement can be applied to, e.g., a proximity switch, by simply changing a threshold value.

In a conventional magnetic detecting apparatus using a simple pickup coil utilizing an electromagnetic induction effect, only a magnetic field which is changed as a function of time in accordance with its measurement principle can be measured. However, by using the saturable magnetic sensor 216, magnetic fields can be measured with high precision in the wide range from a DC magnetic field to a high-frequency magnetic field.

In this embodiment, a degree of deformation (i.e., a change in pulse width) of part of a waveform of the detection signal b of the magnetic sensor 216, which is caused by an external magnetic field, is measured to detect an intensity of the external magnetic field. The waveform itself is substantially free from changes in external conditions such as temperatures. No countermeasure for temperature compensation need be taken for the detection signal b from the magnetic sensor 216.

The present invention is not limited to the particular embodiments described above. In the above embodiments, measurement of the DC external magnetic fields +H2 and -H3 is exemplified. However, the present invention is also applicable to measurement of an AC external magnetic field, as has been described above.

The high-frequency magnetizing signal a having a triangular waveform is used as an AC magnetizing current applied from the magnetizing signal generator 211 to the detection coil 218 of the magnetic sensor 216 through the impedance element 215. However, when the DC external magnetic fields +H2 and -H3 as in the above embodiment are to be measured, sufficiently y high measurement precision can be obtained even if a low-frequency magnetizing current is used. That is, the frequency of the AC magnetizing current applied to the magnetic sensor 216 preferably about 10 times that of the external magnetic field as a target object. However, sufficiently high measurement precision can be obtained depending on target objects without necessarily satisfying the above condition.

In addition, in the above embodiment, the waveform of the AC magnetizing current applied to the detection coil 218 of the magnetic sensor 216 is a triangular wave. However, a sin wave, a saw-tooth wave, a logarithmic wave, or the like having a predetermined RMS may be used.

As described above, according to the magnetic field detecting apparatus of the present invention, an AC magnetizing current having a predetermined RMS is applied to a detection coil of a magnetic sensor to obtain a detection signal. A degree of deformation of part of a waveform of the detection signal in response to an external magnetic field is detected. Therefore, the voltage value of the AC magnetizing electric power applied to the magnetic sensor can be greatly reduced, and the external magnetic field intensity can be easily detected in accordance with the degree of deformation of the signal waveform of the detection signal. As a result, each circuit arrangement can be simplified, and the apparatus as a whole can be made compact at low cost.

In the embodiment shown in FIG. 12, since an AC power is supplied to the coil, power consumption is high, resulting in inconvenience. In particular, the apparatus of this embodiment is not suitably applied to a battery-driven arrangement. For example, in order to check a defect of a long pipeline, a detecting head having a magnetic sensor is inserted into a pipe and is driven without any power cable, thereby checking defects inside the pipe. In this case, since a power source for the detecting head is a battery, the arrangement in the embodiment of FIG. 12 is not suitable for the above application.

FIG. 35 is a block diagram showing a basic arrangement of another magnetic measuring apparatus according to the present invention, which employs a magnetic measuring method thereof. Referring to FIG. 35, reference numeral 301 denotes a pulse voltage generator constituting a pulse voltage supply means. The pulse voltage generator 301 generates positive and negative pulse voltages at predetermined intervals. A series circuit of a resistor 302 serving as a fixed impedance and a coil 303 of a magnetic sensor 303 is connected to the output terminal of the pulse voltage generator 301. The coil 303a is wound around a ferromagnetic core 303b. Positive and negative peak values of the voltage generated across the coil 303a are respectively detected by a pair of peak value detecting means constituted by a positive voltage peak detector 304 and a negative voltage peak detector 305. Peak detection outputs from the peak detectors 304 and 305 are added by an adder 306, thereby obtaining a measurement output Vo.

In the embodiment having the above arrangement, a pulse voltage is supplied from the pulse voltage generator 301 to the coil 303a of the magnetic sensor 303, and the ferromagnetic core 303b is magnetized to a saturation state by this pulse voltage when an external magnetic field as a target object crosses the ferromagnetic core 303b, positive and negative voltages are generated by the coil 303a in correspondence with the polarity and intensity of the external magnetic field. In this case, a peak value V1 of the positive voltage is detected by the positive voltage peak detector 304, and a peak value V2 of the negative voltage is detected by the negative voltage peak detector 305. An addition of V1+(-V2) is performed by the adder 306, thereby generating the measurement output Vo.

Since a pulse voltage is applied to the coil 303a of the magnetic sensor 303, power consumption is lower than that of an arrangement to which an AC power is supplied, thereby achieving effective energy savings. For example, a ratio of a pulse width τ to a pulse period T of the pulse voltage is set to be (10τ to 100τ)=T, the average power supplied to the magnetic sensor 303 can be reduced to about 1/10 to 1/100, so that a battery can be sufficiently used as a power source.

Since the peak values of the voltage generated across the coil 303a are detected, even if the ratio T/τ is changed in a wide range of 2 to 100, the relative sensitivity of the detection sensitivity for the minute magnetic flux is not almost changed, as indicated in a graph I of FIG. 36. To the contrary, in the amplitude detection system shown in FIG. 12, as indicated by a graph II of FIG. 36, the sensitivity is abruptly decreased when the ratio T/τ is 5 or more. Therefore, it is apparently difficult to achieve energy savings.

Figure 37:
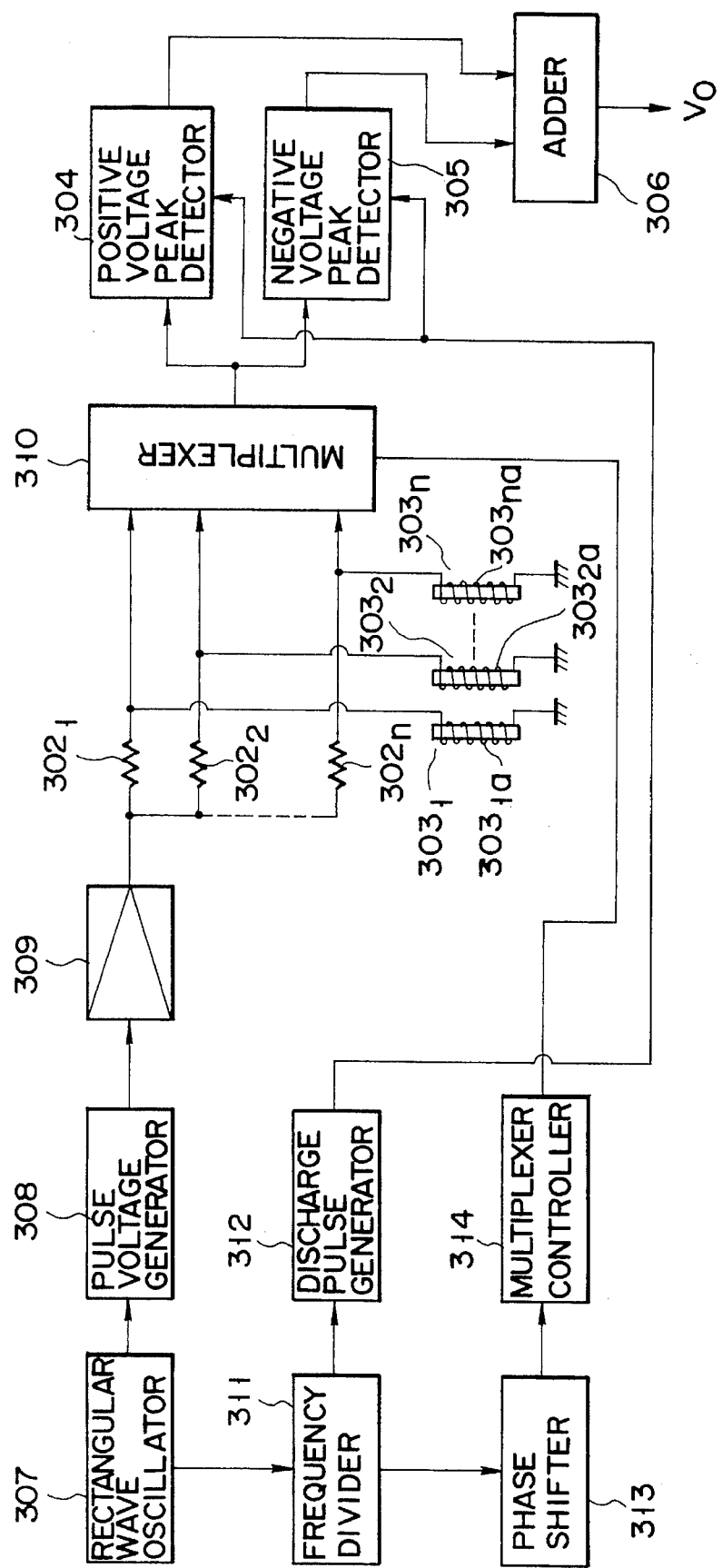
FIG. 37 is a block diagram showing still another embodiment of the present invention.
Figure 38:
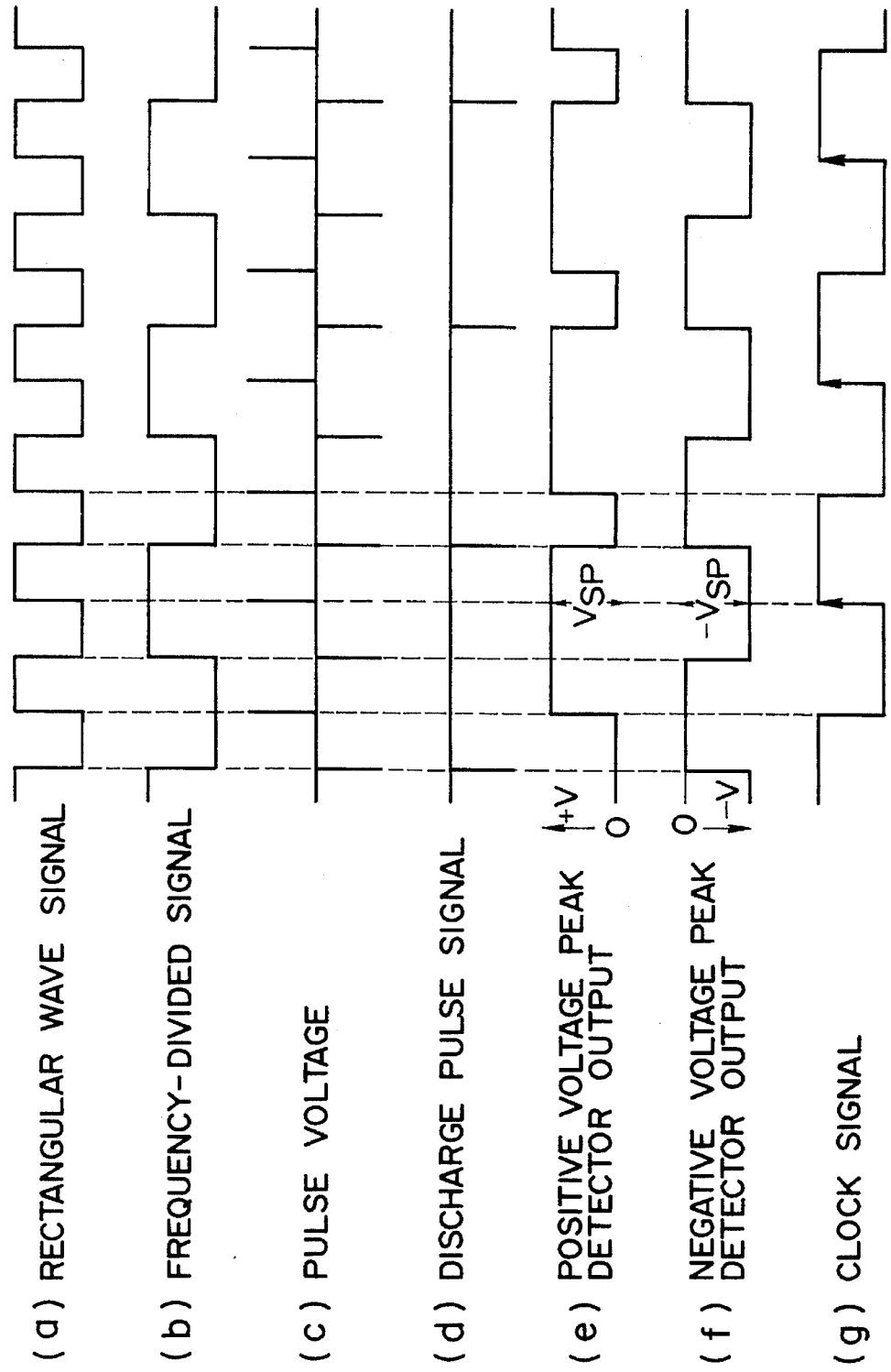
FIG. 38 is an output waveform chart of the respective components in the embodiment shown in FIG. 37.
Figure 46:
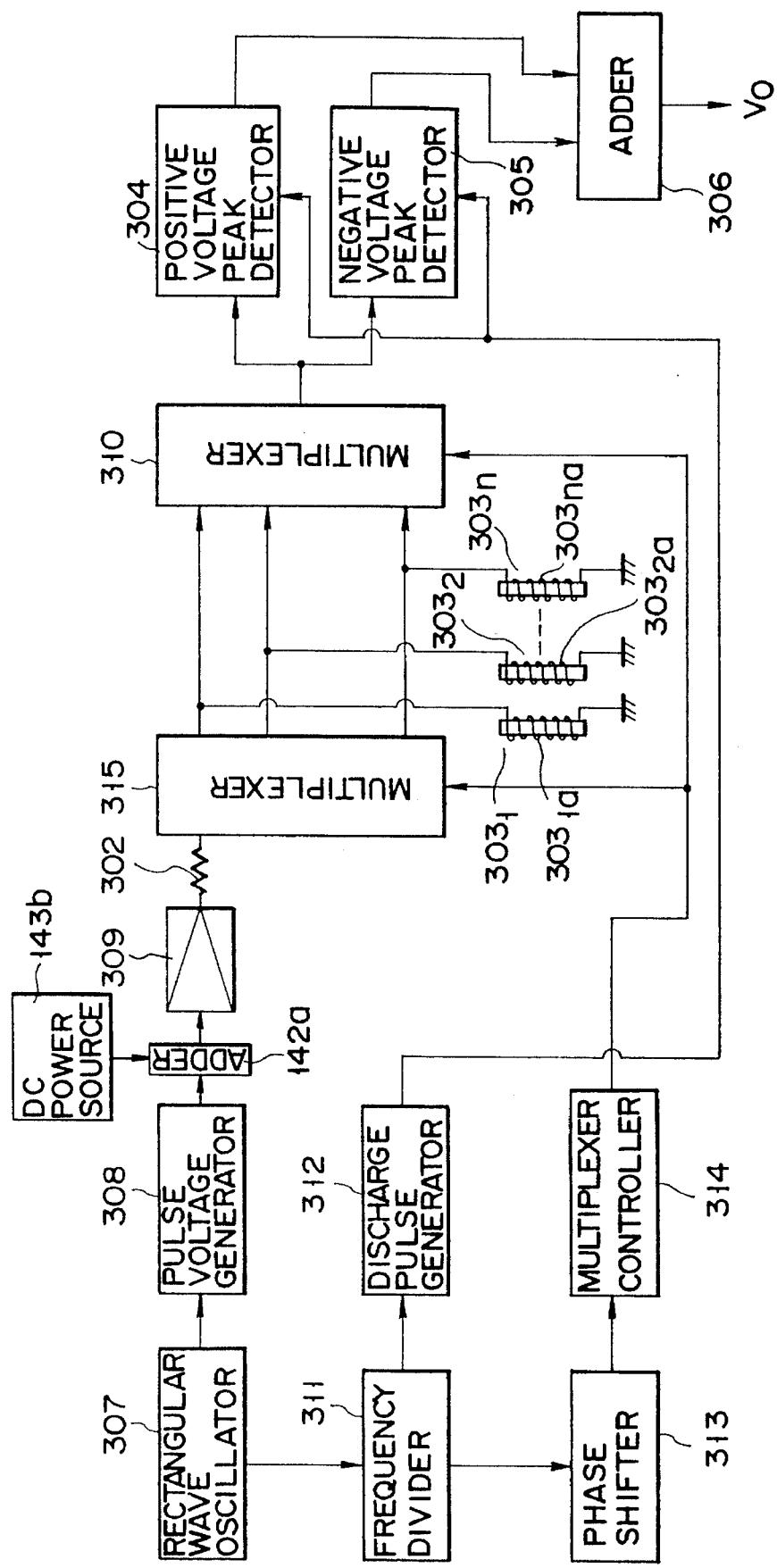
Figure 48:
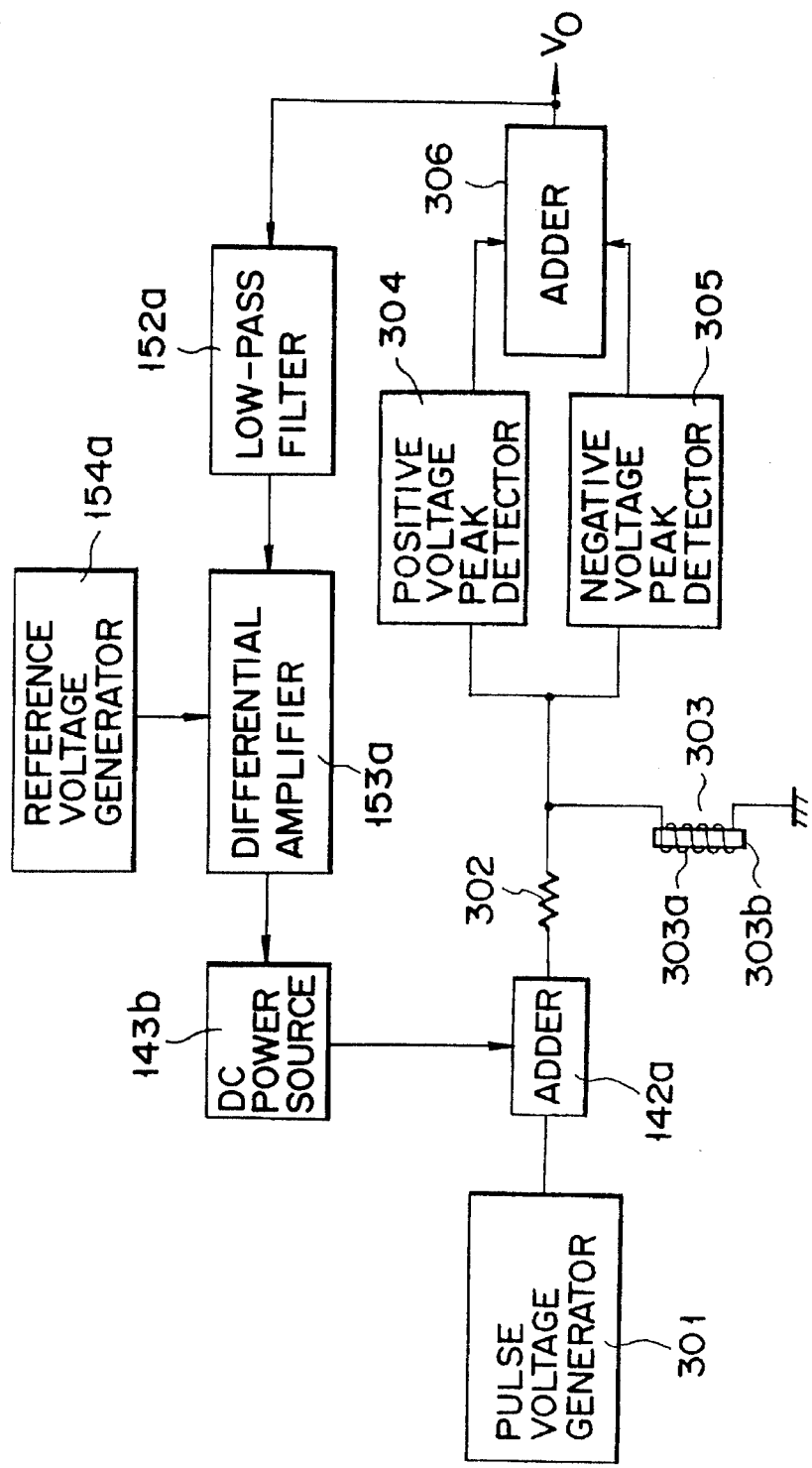
Figure 55:
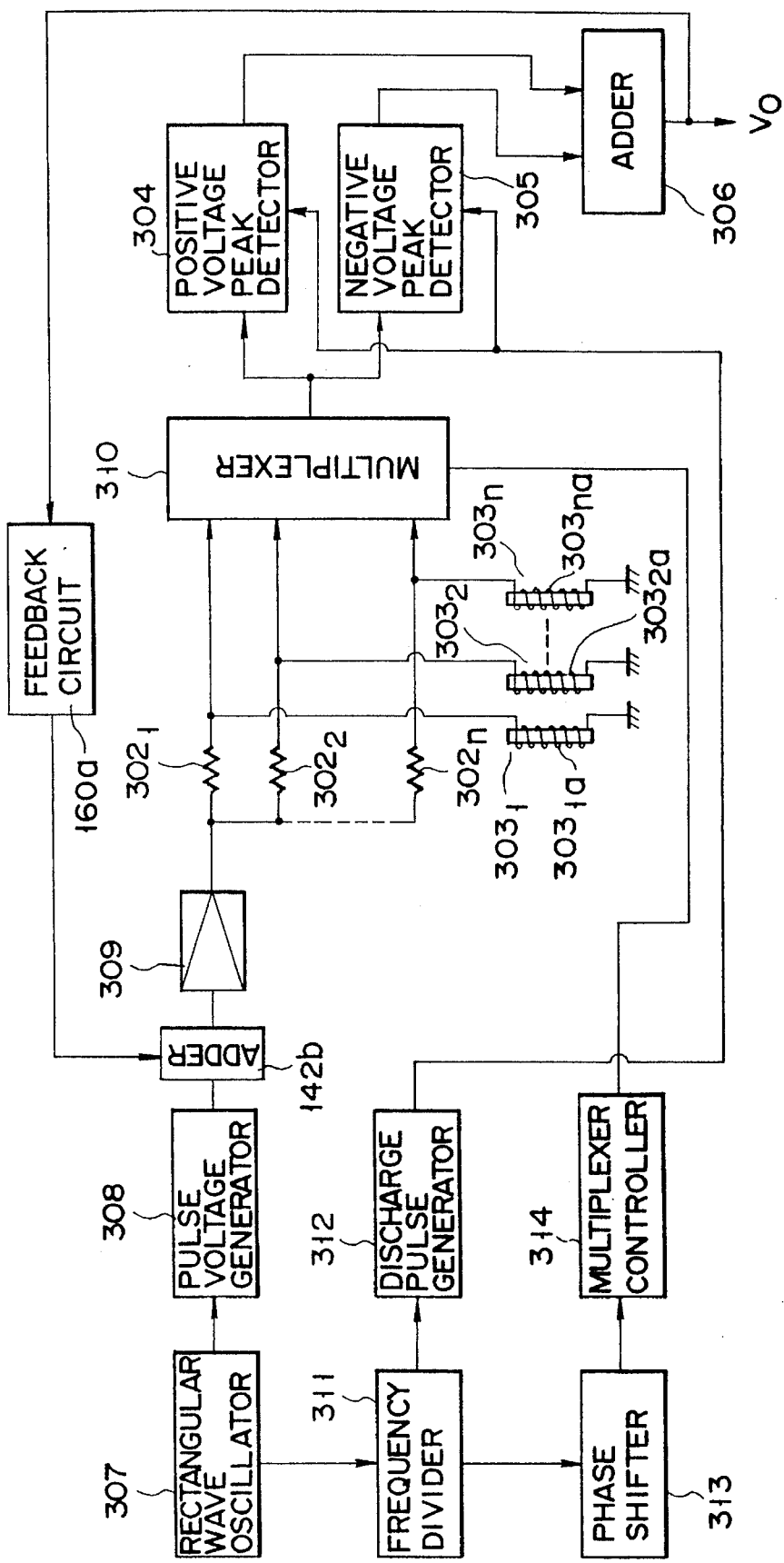

FIG. 37 is a block diagram showing a basic arrangement of a magnetic field measuring apparatus according to still another embodiment of the present invention. The same reference numerals as in FIG. 35 denote the same parts in FIG. 37, and a detailed description thereof will be omitted. In the apparatus of the embodiment shown in FIG. 37, a pulse voltage supply source comprises a rectangular wave oscillator 307, a pulse voltage generator 308, and a pulse power amplifier 309. The rectangular wave oscillator 307 generates a rectangular wave signal shown in FIG. 38(a). The pulse voltage generator 308 generates positive and negative pulse voltages at predetermined intervals, as shown in FIG. 38(c), in synchronism with leading and trailing edges of the rectangular wave signal. These pulse voltages are amplified by a pulse power amplifier 309, and the amplified voltages are output.

N magnetic sensors $303_1, 303_2, \ldots 303_n$ are arranged, and coils $303_{1a}, 303_{2a}, \ldots, 303_{na}$ of the magnetic sensors $303_1, 303_2, \ldots, 303_n$ are commonly connected to the output terminal of the pulse power amplifier 309, respectively, through resistors $302_n, 302_2, \ldots, 302_n$. Coil terminal voltages across the magnetic sensors $303_1$ to $303_n$ are supplied to a multiplexer 310 serving as a selecting means. The multiplexer 310 sequentially and alternatively supply the voltages generated by the coils $303_{1a}$ to $303_{na}$ to the positive and negative voltage peak detectors 304 and 305. The peak detectors 304 and 305 sequentially detect the peak values of the output voltages from the coils $303_{1a}$ to $303_{na}$ and supply detection signals shown in FIGS. 38(e) and 38(f) to the adder 306.

A rectangular wave signal from the rectangular wave oscillator 307 is supplied to a frequency divider 311. The frequency divider 311 performs ½ frequency division, thereby obtaining a frequency-divided signal shown in FIG. 38(b). The frequency-divided signal is supplied to a discharge pulse generator 312 and a phase shifter 313. The discharge pulse generator 312 generates a discharge pulse signal synchronized with a leading edge of the frequency-divided signal input as shown in FIG. 38(d) and supplies the discharge pulse signal to the peak detectors 304 and 305, thereby clearing the output voltage of each detector to zero. The phase shifter 313 shifts the input frequency-divided signal through 90°. The 90°-shifted signal is supplied to a multiplexer controller 314. The multiplexer controller 314 generates a clock signal (FIG. 38(g)) synchronized with the signal from the phase 71574 shifter 313 and supplies this clock signal to the multiplexer 30. The multiplexer 310 is controlled by this clock signal and performs a selection operation.

In the embodiment having the above arrangement, the positive and negative pulse voltages are generated by the pulse voltage generator 308, and these pulse voltages are amplified by the pulse power amplifier 309 and are supplied to the coils $303_{1a}$ to $303_{na}$ of the magnetic sensors $303_1$ to $303_n$ through the resistors $302_1$ to $302_n$, respectively.

Meanwhile, the multiplexer 310 is controlled by a clock signal from the multiplexer controller 314 to sequentially and alternatively extract voltages generated by the coils $303_{1a}$ to $303_{na}$ and the extracted voltages are supplied to the peak detectors 304 and 305. The peak values of the voltages generated by the coils $303_{1a}$ to $303_{na}$ are sequentially supplied from the peak detectors 304 and 305 to the adder 306, thereby obtaining a measurement output as a sum of outputs from the magnetic sensors $303_1$ to $303_n$. In this manner, even if a large number of magnetic sensors are used, the pulse voltage is supplied to the coil of each magnetic sensor. Therefore, the amount of power consumed by all the magnetic sensors is small.

Even if a large number of magnetic sensors are used, they can be driven with a battery. In a conventional arrangement using an AC power, when a large number of magnetic sensors are used, a large amount of power is required, so that a large-capacity amplifier and the like must be used. In this embodiment, however, the capacity of the pulse power amplifier 309 can be small. This embodiment is particularly suitable for checking defects of long pipelines without using any power cable.

FIG. 39 is a block diagram of a magnetic flux measuring apparatus according to still another embodiment of the present invention. The same reference numerals as in FIG. 37 denote the same parts in FIG. 39, and a detailed description thereof will be omitted. In the apparatus of the embodiment shown in FIG. 39, one resistor 302 is used as a fixed impedance, and a pulse voltage from a pulse power amplifier 309 is supplied to a multiplexer 315 different from a multiplexer 310 through the resistor 302. Coils $303_{1a}$ to $303_{na}$ of magnetic sensors $303_1$ to $303_n$ are commonly connected to the output terminal of the multiplexer 315. The multiplexer 315 is similarly controlled by a clock signal from a multiplexer controller 314 as in the multiplexer 310.

In this embodiment having the above arrangement, pulse signals are sequentially and alternatively supplied to the coils $303_{1a}$ to $330_{na}$ of the magnetic sensors $303_1$ to $303_n$ by the multiplexer 315. The voltages generated by the coils $303_{1a}$ to $303_{na}$ of the magnetic sensors $303_1$ to $303_n$ are sequentially and alternatively extracted by the multiplexer 310. Therefore, even if the large number of magnetic sensors $303_1$ to $303_n$ are used, only one magnetic sensor is operated each time. That is, when the pulse voltage is supplied to the magnetic sensor $303_1$ by the multiplexer 315, a voltage generated by the coil $303_{1a}$ of the magnetic sensor 3031 is extracted by the multiplexer 310.

The power consumption can be further reduced in the apparatus of this embodiment, and the capacity of the pulse power amplifier 309 can be further reduced.

In this embodiment as has been described in detail, the detection sensitivity for the minute magnetic field can be increased, and the coil of the magnetic sensor is driven with a pulse voltage to achieve energy savings. For example, the magnetic measuring method and the apparatus embodying the same according to the present invention are very effective to obtain a battery-driven arrangement such as a pipeline inspection apparatus called "PLG". In addition, even if a large number of magnetic sensors are used, the coil of each magnetic sensor is driven with a pulse voltage. Voltages generated by the respectively coils are sequentially and alternatively extracted to achieve energy savings. Therefore, this embodiment is particularly effective for a battery-driven arrangement.

FIGS. 40, 41 and 42 are block diagrams of other embodiments of the present invention, respectively. These embodiments can be obtained by modifying the embodiments in FIGS. 12, 17 and 18 correspondingly to the embodiment in FIG. 20. More particularly, the resistor 22 in FIG. 12 is replaced with a second coil 22a and a second ferromagnetic core 22b in FIG. 40. In FIG. 41, a second coil 22a and a second ferromagnetic core 22b are used instead of the resistor 22 in FIG. 17. The resistor 22 in FIG. 18 is also replaced with a second coil 22a and a second ferromagnetic core 22b in FIG. 42. The operational principles of these embodiments are identical to that of the embodiment of FIG. 20.

FIGS. 43, 44 45 and 46 are block diagrams of another embodiments of the present invention, respectively. These embodiments can be obtained by modifying the embodiments in FIGS. 17, 18, 35 and 39 as variations according to the embodiment in FIG. 28. The embodiment in FIG. 43 can be realized by adding a DC power source 143b, an adder 142a and a power amplifier 144a to the embodiment of FIG. 17. More particularly, the adder 142a and the amplifier 144a are connected between the oscillator 21 and the resistor 22. The power source 143b supplies the DC power to the adder 142a. In FIG. 44, a DC power source 143b, an adder 142a and a amplifier 144a are also inserted between the oscillator 21 and the resistor 22 in FIG. 18. In FIG. 45, an adder 142a is added between the pulse voltage generator 301 and the resistor 302, and a DC power source 143b is connected to the adder 142a. Also in FIG. 46, an adder 142a is inserted between the pulse voltage generator 308 and the amplifier 309, and a DC power source 143b supplies a DC power.

FIGS. 47, 48, 49, and 50 are block diagrams of another embodiments of the present invention, respectively. Such embodiments can be obtained as variations based on the embodiment in FIG. 30. The embodiments in FIGS. 47, 48, 49 and 50 correspond to the embodiments in FIGS. 18, 35, 49 and 50, respectively. A low-pass filter 152a, a differential amplifier 153a, a DC power source 143b, a reference voltage generator 154a and an adder 142a are included in all embodiments, and an amplifier 144a is further included in the embodiments in FIGS. 47 and 49.

FIGS. 51, 52, 53, 54, 55, and 56 are blocks diagrams of another embodiments of the present invention, respectively. In accordance with the embodiment in FIG. 31, the embodiments in FIGS. 17, 18, 33, 35, 37 and 39 are modified as variations by including a feedback loop. More particularly, in FIGS. 51, 52 and 54, the feedback loop is composed of a feedback circuit 160a and an adder 142b, and an amplifier 144b is further included. In FIG. 53, the digital output signal of the counter 220 is fed through a D/A converter 220a to a feedback circuit 160a.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A minute magnetic flux measuring apparatus which is capable of detecting high frequency components of a magnetic flux with a high speed operation, without using an integrator circuit, comprising:

a coil wound around one ferromagnetic core;

an AC power source for applying an AC current of a predetermined frequency to said coil through a fixed impedance until said ferromagnetic core is saturated and for producing an AC voltage across said coil, said AC current and said AC voltage each having alternating positive and negative waveform portions;

means connected directly to said coil for independently detecting an amplitude of a positive waveform portion of the produced AC voltage and an amplitude of a negative waveform portion of the produced AC voltage;

comparing means for comparing the detected amplitude of the positive waveform portion with the detected amplitude of the negative waveform portion, and for producing a comparison result signal; and outputting means for outputting a voltage corresponding to a DC component of said comparison result signal, said DC component corresponding to the external magnetic flux crossing said coil.

2. An apparatus according to claim 1, wherein:

said comparing means produces a difference voltage between said compared detected positive waveform portion and detected negative waveform portion, said comparison result signal corresponding to said difference voltage; and said outputting means outputs a voltage corresponding to a DC component of said difference voltage produced by said comparing means.

3. An apparatus according to claim 1, wherein:

said comparing means includes means for comparing a duration of the detected positive waveform portion of the AC voltage with that of the detected negative waveform portion of the AC voltage, and for producing said comparison result signal as a comparison output voltage; and said outputting means comprises means for measuring said comparison output voltage from said comparing means and for outputting a voltage corresponding to the external magnetic flux crossing said coil.

4. An apparatus according to claim 1, wherein said apparatus comprises only a single ferromagnetic core.

5. An apparatus according to claim 1, wherein said AC current is an AC pulse current of predetermined frequency, and wherein said AC voltage is an AC pulse voltage.

6. An apparatus according to claim 5, wherein said comparing means comprises a pair of peak value detecting means for respectively detecting positive and negative peak values.

7. An apparatus according to claim 5, wherein said fixed impedance comprises a second coil wound around said one ferromagnetic core.

8. An apparatus according to claim 5, wherein said power source for applying said pulse current comprises a rectangular wave generator and a differentiator coupled to said rectangular wave generator.

9. An apparatus according to claim 5, further comprising:

a low-pass filter, coupled to said outputting means, for filtering said voltage corresponding to the external magnetic flux crossing said coil; and means for negatively feeding back a current corresponding to an output of said low-pass filter.

\* \* \* \* \*